United States Patent
Nakano et al.

(10) Patent No.: US 8,486,122 B2
(45) Date of Patent: Jul. 16, 2013

(54) DEVICE FOR REMOVAL OF INTERMAXILLARY FIXATION

(75) Inventors: Makoto Nakano, Hiroshima (JP); Toshio Sugahara, Okayama (JP); Takeshi Furuya, Sasayama (JP)

(73) Assignees: Furuya Industrial Co., Ltd., Sasayama-shi, Hyogo (JP); Makoto Nakano, Hiroshima-shi, Hiroshima (JP)

( * ) Notice: Subject to any disclaimer, the term of this patent is extended or adjusted under 35 U.S.C. 154(b) by 0 days.

(21) Appl. No.: 12/521,207

(22) PCT Filed: Dec. 19, 2007

(86) PCT No.: PCT/JP2007/074388
§ 371 (c)(1),
(2), (4) Date: Nov. 6, 2009

(87) PCT Pub. No.: WO2008/081716
PCT Pub. Date: Jul. 10, 2008

(65) Prior Publication Data
US 2010/0055632 A1    Mar. 4, 2010

(30) Foreign Application Priority Data
Dec. 28, 2006 (JP) ................................. 2006-354200

(51) Int. Cl.
*A61B 17/24* (2006.01)
(52) U.S. Cl.
USPC ........................................................ 606/322
(58) Field of Classification Search
USPC .................... 433/2, 21, 22, 24, 8–19; 606/53, 606/54, 308, 324, 328, 331, 300–306; 602/5, 602/17, 902; 128/848, 859–862; 27/21.1; 24/129 R, 115 F
See application file for complete search history.

(56) References Cited

U.S. PATENT DOCUMENTS 3,530,583 A * 9/1970 Anderson et al. ............... 433/11
4,639,219 A 1/1987 Gagin
(Continued)

FOREIGN PATENT DOCUMENTS

| JP | 61-14011 U | 1/1986 |
| JP | 5-15547 A | 1/1993 |

(Continued)

OTHER PUBLICATIONS

English Translation of JP-2006/167275.*

(Continued)

*Primary Examiner* — Cris L Rodriguez
*Assistant Examiner* — Justin O'Donnell
(74) *Attorney, Agent, or Firm* — Westerman, Hattori, Daniels & Adrian, LLP

(57) ABSTRACT

There is provided an intermaxillary fixation releasing device in which intermaxillary fixation can be released without a special tool, and the labor of the practitioner and the burden on the patient are reduced. The intermaxillary fixation releasing device comprises a maxillary joint composed of a first synthetic resin; a mandibular joint composed of a second synthetic resin; and a connector composed of an elastomer, wherein the maxillary joint is provided with an upper-side interlocking part and an upper-side support part; the mandibular joint is provided with a lower-side interlocking part and a lower-side support part; the elastomer forming the connector is incompatible or substantially incompatible with the first synthetic resin and the second synthetic resin; and the maxillary joint and the mandibular joint are joined with the connector in a state in which the upper-side support part and the lower-side support part are embedded in the connector.

5 Claims, 15 Drawing Sheets

U.S. PATENT DOCUMENTS

| | | | |
|---|---|---|---|
| 4,708,646 A * | 11/1987 | Jasper | 433/19 |
| 5,306,142 A * | 4/1994 | Richards | 433/22 |
| 6,488,498 B1 * | 12/2002 | Mariani, Jr. | 433/11 |
| 6,746,243 B1 * | 6/2004 | Holzhauer | 433/15 |
| 6,884,067 B2 * | 4/2005 | Tuneberg | 433/19 |
| 6,887,076 B2 * | 5/2005 | Graham | 433/19 |
| 6,910,885 B2 * | 6/2005 | Bloore et al. | 433/15 |
| 8,062,032 B2 * | 11/2011 | Bulloch et al. | 433/18 |
| 2004/0081937 A1 | 4/2004 | Graham | |
| 2004/0096798 A1 * | 5/2004 | Cleary | 433/18 |
| 2006/0073434 A1 * | 4/2006 | Reynolds | 433/18 |

FOREIGN PATENT DOCUMENTS

| | | |
|---|---|---|
| JP | 8-206135 A | 8/1996 |
| JP | 2006-167275 A | 6/2006 |
| JP | 2007-14595 A | 1/2007 |

OTHER PUBLICATIONS

Tamari et al, "An easily and immediately releasable intermaxillary fixation appliance for use after the correction of surgical orthognathic cases of jaw deformity or fracture," The Journal of Japan Orthodontic Society, Dec. 1988, pp. 811-814.*

Watanabe et al, "The removable inter-maxillary fixating appliance used after the operation of the surgical orthodontic correction cases," The Journal of Japan Orthodontic Society, Mar. 1985, pp. 160-164.*

International Search Report of PCT/JP2007/074388, Mailing Date of Feb. 19, 2008.

* cited by examiner

F-F

G-G

DEVICE FOR REMOVAL OF INTERMAXILLARY FIXATION

TECHNICAL FIELD

The present invention relates to a device for removal of intermaxillary fixation, the device being used when intermaxillary fixation is implemented in medical procedures and the like.

BACKGROUND ART

Intermaxillary fixation is performed in order to keep a jawbone immobile and in a correct position when orthodontic surgery is carried out for a maxillary fracture repositioning, jaw deformities, and the like. Intermaxillary fixation is carried out by fixing the upper and lower jaws using a metal wire or another ligature wire. Intermaxillary fixation is preferably performed as soon as possible following injury or surgery. However, there are cases in which the respiratory tract becomes blocked by vomiting, hemorrhaging, intraoral swelling, or the like following injury. When the respiratory tract is blocked, oxygen deficiency may cause irreversible brain damage in four to six minutes and there is danger of death when such a state remains unresolved for 10 to 15 minutes or longer. Therefore, the respiratory tract must be cleared immediately. Since a patient with intermaxillary fixation cannot open the mouth, the intermaxillary fixation must be rapidly released and the respiratory tract cleared.

The intermaxillary fixation is released by cutting the ligature wire fixing the upper and lower jaws using wire-cutting scissors or the like. However, medical personnel are not necessarily near a patient with a blocked respiratory tract, and the respiratory tract must be cleared in a very short period of time. It is therefore preferred that the intermaxillary fixation be released by a person in the vicinity. However, there is a problem in that it is very unlikely that the intermaxillary fixation can be released using wire-cutting scissors or another tool when a person who does not have any knowledge of intermaxillary fixation removal encounters a patient with a blocked respiratory tract.

In view of the above, various devices for releasing intermaxillary fixation have conventionally been proposed in order to rapidly release intermaxillary fixation without a tool even if the person does not have knowledge about releasing intermaxillary fixation.

In Prior Art 1, an arch wire is mounted on the upper and lower jaws, a hook is provided so as to straddle the arch wire, and the upper and lower jawbones are fixed. The hook is formed using a hard metal wire. A holding part is formed on the hook and the intermaxillary fixation is released by pulling the holding part outward from the mouth (e.g., see non-patent document 1).

In Prior Art 2, first, ordinary intramaxillary fixation is performed in the upper and lower jaws. A gap is formed in the vertical direction between the surface of the teeth and intramaxillary fixation means. A loop is formed by passing through the gap a ligature wire that is disposed between the upper and lower jaws, and an interlocking unit is passed through the loop. The interlocking unit is a metal wire having a thickness that prevents passage through the gap. Intermaxillary fixation can be set by applying tension to the ligature wire in order to hold the interlocking unit in place. In the case that the intermaxillary fixation is to be released, the holding part formed on the interlocking unit is pulled outward from the mouth, whereby the interlocking unit moves along the row of teeth, the interlocking unit is sequentially released from the ligature wire loop, and the intermaxillary fixation is released (e.g., see non-patent document 2).

Non-patent Document 1: Yasoo Watanabe et al., "Removable Device for Intermaxillary Fixation Following Orthodontic Surgery," The Japanese Journal of Orthodontics, 1985, V44, p. 160-164.

Non-patent Document 2: Kazuhiko Tamari et al., "Instantly Releasable Device for Intermaxillary Fixation Following Orthodontic Surgery and Jawbone Fracture Repositioning," The Japanese Journal of Orthodontics, 1988, V47, p. 811-814.

DISCLOSURE OF THE INVENTION

Problems the Invention is to Solve

However, Prior Art 1 has the following problems.

The device for removal of intermaxillary fixation must be fabricated for each patient. This is because a pre-manufactured product cannot be modified to suit differences between individual patients. Also, the intermaxillary fixation releasing device is composed of various small components. The fabrication is very laborious in that the practitioner must assemble and fabricate the components for each patient.

An intermaxillary fixation releasing device exerts an intermaxillary fixation force and must be adjusted so as to allow the intermaxillary fixation to be released. This is due to the fact that releasing of the intermaxillary fixation is not possible when priority is placed on the intermaxillary fixation force, and sufficient intermaxillary fixation force cannot be applied when priority is placed on releasing the intermaxillary fixation. The fabrication, mounting, and adjustment of the intermaxillary fixation releasing device also depend considerably on the skill and experience of the practitioner. The adjustment must be performed in advance outside the oral cavity of the patient, and preparation requires a considerable amount of time. Adjustment inside the oral cavity is also required and this also requires a considerable amount of time.

The burden on the patient is considerable because it is also necessary to make adjustments in the oral cavity of the patient when the intermaxillary fixation releasing device is mounted. A considerable burden is placed on the patient while the intermaxillary fixation releasing device is being mounted because the holding part and other components of the intermaxillary fixation releasing device are large, and the patient feels discomfort when contact is made with the gums and backside of the lips (the surface of the mucous membrane of the lips).

The intermaxillary fixation releasing device has a holding part disposed near the gums, so the holding part becomes hidden behind the lips and is not visible from outside of the mouth. Although a special tool is not required for removal, the intermaxillary fixation cannot be removed if a person in the vicinity of the patient does not notice the holding part. Even when the holding part can be seen, it is unlikely that the intermaxillary fixation can be removed when it is not understood that the intermaxillary fixation can be removed by pulling the holding part.

Prior Art 2 has the following problems.

The intermaxillary fixation releasing device is not required to be fabricated for each patient, but fabrication in advance is required and is laborious.

The intermaxillary fixation releasing device must be adjusted and the adjustment is difficult. Adjustment is required so that an intermaxillary fixation force is applied and so that the intermaxillary fixation can be released.

The intermaxillary fixation releasing device requires adjustment so that an intermaxillary fixation force is applied and so that the intermaxillary fixation can be released. The fabrication, mounting, and adjustment of the intermaxillary fixation releasing device also depend considerably on the skill and experience of the practitioner. More particularly, confirmation of whether the intermaxillary fixation can be released is not possible without dismantling the intermaxillary fixation releasing device.

The intermaxillary fixation releasing device is mounted in a completely different from ordinary intermaxillary fixation means, and the practitioner must be skilled.

The burden on the patient is considerable in that the practitioner must spend considerable time performing a large amount of work inside the oral cavity of the patient when the intermaxillary fixation releasing device is mounted. Also, a considerable burden is placed on the patient while the intermaxillary fixation releasing device is being mounted because the holding part and other components of the intermaxillary fixation releasing device are large, and the patient feels discomfort when contact is made with the gums and backside of the lips (the surface of the mucous membrane of the lips).

The intermaxillary fixation releasing device has a holding part disposed near the gums, so the holding part becomes hidden behind the lips and is not visible from outside of the mouth. Although a special tool is not required for removal, the intermaxillary fixation cannot be removed if a person in the vicinity of the patient does not notice the holding part. Even when the holding part can be seen, it is unlikely that the intermaxillary fixation can be removed when it is not understood that the intermaxillary fixation can be removed by pulling the holding part. In the case that all of the ligature wires are retained and secured using a single interlocking unit and are then to be released, there is a possibility that the interlocking unit will hang on the intramaxillary fixation means, the loop of the ligature wire will not release from the interlocking unit, and the intermaxillary fixation cannot be released.

Accordingly, in Prior Art 1 and 2, the fabrication, mounting, and adjustment of the intermaxillary fixation releasing device also depend considerably on the skill and experience of the practitioner. Also, a considerable burden is placed on the patient. On the other hand, the practitioner cannot sense whether the intermaxillary fixation is more likely to be released. Accordingly, there is a problem in that the intermaxillary fixation releasing device is not used in patients that require intermaxillary fixation.

Furthermore, in the intermaxillary fixation releasing device of Prior Art 1 and 2, there is a possibility that even a person knowledgeable of only common intermaxillary fixation releasing methods cannot remove the intermaxillary fixation releasing device without knowledge of the releasing method. A person knowledgeable of only common intermaxillary fixation releasing methods knows to cut the wire as an ordinary procedure, and there is therefore a risk that the same wire cutting method will be attempted in order to release the intermaxillary fixation. Cutting is not possible even if such cutting means is used in Prior Arts 1 and 2, and the cutting operation involves a risk.

The present invention was contrived in view of the problems described above, and an object thereof is to provide an intermaxillary fixation releasing device in which the labor of the practitioner is reduced, the device can be used regardless of the skill and experience of the practitioner, the burden on the patient can be reduced, there is a high possibility that the device can be removed without the use of a special tool even by a person without any knowledge of intermaxillary fixation removal, and a person versed in only common intermaxillary fixation release methods can release the intermaxillary fixation by cutting a wire in a conventional manner. The use of an intermaxillary fixation releasing device can thereby be recommended for a patient requiring intermaxillary fixation, and the safety of medical treatment can accordingly be enhanced.

Means of Solving the Problems

The present inventor found that, in order achieve the objects described above, it is necessary to provide a practitioner with an intermaxillary fixation releasing device as a ready-made product rather than having the practitioner individually fabricate the intermaxillary fixation releasing device, and that it is advantageous to dispose a intermaxillary fixation releasing device between the jaws of the patient. The present inventor also found that synthetic resins that are mutually incompatible or synthetic resins that are substantially incompatible with each other can exhibit a fixed adhesive strength and have properties that readily allow separation.

In view of the above, the device for removal of intermaxillary fixation according to a first aspect comprises a maxillary joint (2) composed of a first synthetic resin; a mandibular joint (3) composed of a second synthetic resin; and a connector (4) composed of an elastomer, wherein the maxillary joint (2) is provided with an upper-side interlocking part (21) and an upper-side support part (22); the mandibular joint (3) is provided with a lower-side interlocking part (31) and a lower-side support part (32); the elastomer forming the connector (4) is incompatible or substantially incompatible with the first synthetic resin and the second synthetic resin; and the upper-side support part (22) and the lower-side support part (32) are joined with the connector (4). In the present invention, the scope includes the first synthetic resin and the second synthetic resin being the same synthetic resin.

The device for removal of intermaxillary fixation according to a second aspect comprises a maxillary joint (2) composed of a first synthetic resin; a mandibular joint (3) composed of a second synthetic resin; and a connector (4) composed of an elastomer, the device for removal of intermaxillary fixation characterized in that the maxillary joint (2) is provided with an upper-side interlocking part (21) and an upper-side support part (22); the mandibular joint (3) is provided with a lower-side interlocking part (31) and a lower-side support part (32); the elastomer forming the connector (4) is incompatible or substantially incompatible with the first synthetic resin and the second synthetic resin; and the upper-side support part (22) and the lower-side support part (32) are embedded in the connector (4), and the upper-side support part (22) and the lower-side support part (32) are joined.

The device for removal of intermaxillary fixation, according to a second aspect comprises a maxillary joint (2) composed of a first synthetic resin; a mandibular joint (3) composed of a second synthetic resin; and a connector (4) composed of an elastomer, wherein the maxillary joint (2) is provided with an upper-side interlocking part (21) and an upper-side support part (22); the mandibular joint (3) is provided with a lower-side interlocking part (31) and a lower-side support part (32); the elastomer forming the connector (4) is incompatible or substantially incompatible with the first synthetic resin and the second synthetic resin; and the upper-side support part (22) and the lower-side support part (32) are in contact, and the upper-side support part (22) and the lower-side support part (32) are joined with the connector (4).

The device for removal of intermaxillary fixation according to a fourth aspect comprises a maxillary joint (2) composed of a first synthetic resin; a mandibular joint (3) composed of a second synthetic resin; and a connector (4) composed of an elastomer, wherein the maxillary joint (2) is provided with an upper-side interlocking part (21) and an upper-side support part (22); the mandibular joint (3) is provided with a lower-side interlocking part (31) and a lower-side support part (32); the elastomer forming the connector (4) is incompatible or substantially incompatible with the first synthetic resin and the second synthetic resin; and the upper-side support part (22) and the lower-side support part (32) are in contact, the upper-side support part (22) and the lower-side support part (32) are embedded in the connector (4), and the upper-side support part (22) and the lower-side support part (32) are joined.

The device for removal of intermaxillary fixation according to a fifth aspect is the device for removal of intermaxillary fixation according the first aspect, characterized in that the connector (4) is provided with a connector attaching part (45) on an intraoral surface thereof; the maxillary joint (2) is provided with a maxillary joint attaching part (26) on an upper-side support part (22); the upper-side interlocking part (21) is provided with an insertion hole (25) in the lengthwise direction; a bottom surface (210) of the upper-side interlocking part (21) is the contact surface with the center upper surface of the connector, and an inner surface (220) of the upper-side support part (22) is the contact surface with the intraoral surface (42) of the connector (4); the mandibular joint (3) is provided with a mandibular joint attaching part (36) on the lower-side support part (32); the lower-side interlocking part (31) is provided with and insertion hole (35) in the lengthwise direction; and an upper surface (310) of the lower-side interlocking part (31) is the contact surface with the center lower surface of the connector, and an inner surface (320) of the lower-side support part (32) is the contact surface on the intraoral surface (42) of the connector (4).

The device for removal of intermaxillary fixation according to a sixth aspect has the configuration of any of the first through fifth aspects, wherein the connector (4) is formed from a core part (46) and a tongue-shaped holding part (41) at the two ends of the core part (46).

The device for removal of intermaxillary fixation according to a seventh aspect has the configuration of any of the first through fifth aspects, wherein the extraoral surface (43) of the connector (4) is provided with a display part (44) for displaying characters, drawings, symbols, or the like for intermaxillary fixation releasing instructions or other information.

The device for removal of intermaxillary fixation according to an eighth aspect has the configuration of the sixth aspect, wherein the extraoral surface (43) of the connector (4) is provided with a display part (44) for displaying characters, drawings, symbols, or the like for intermaxillary fixation releasing instructions or other information.

Effects

Therefore, according to the invention of the first aspect, the elastomer forming the connector (4) is incompatible or substantially incompatible with the first synthetic resin and the second synthetic resin. Accordingly, the maxillary joint (2) and the mandibular joint (3) are set in a state in which the upper-side support part (22) and the lower-side support part (32) are mounted on the connector (4), which is in a molten state in the manufacturing process, when the upper-side support part (22) and the lower-side support part (32) are joined with the connector (4). Subsequent cooling yields a state of complete joining with respect to the connector (4), but the upper-side support part (22) of the maxillary joint (2) and the lower-side support part (32) of the mandibular joint (3) are not completely integrated.

The maxillary joint (2) and the mandibular joint (3) are joined with the connector (4) that is composed of an elastomer, the counterpart surfaces of the maxillary joint (2) and the connector (4) assume an adhered state, the counterpart surfaces of the mandibular joint (3) and the connector (4) assume an adhered state, and a fixed level of adhesive force is exhibited.

In the adhering state, when an external force acts on the maxillary joint (2) and the connector (4) as well as the mandibular joint (3) and the connector (4), and a vertical external force acts on the counterpart surfaces; i.e., when an external force is applied in the direction that separates the counterpart surfaces, the adhesive strength will ensure that the counterpart surfaces will not peel away, as long as the external force is less than a fixed strength. However, counterpart surfaces will peel away when the external force is of a fixed level or greater.

In the adhering state, when an external force acts on the maxillary joint (2) and the connector (4) as well as the mandibular joint (3) and the connector (4), and a horizontal external force acts on the counterpart surfaces, i.e., when an external force is applied in the direction that offsets the counterpart surfaces, the adhesive strength ensures that the counterpart surfaces will not peel away, as long as the external force is less than a fixed strength. However, the counterpart surfaces will peel away when the external force is of a fixed level or greater.

Accordingly, the maxillary joint (2), the mandibular joint (3), and the connector (4) do not separate from each other when an external force of less than a fixed strength is applied, but will separate from each other when an external force equal to or greater than a fixed level is applied.

An upper-side interlocking part (21) connected to a maxillary fixation source (9) is formed on the maxillary joint (2), a lower-side interlocking part (31) connected to a mandibular fixation source (9) is formed on the mandibular joint (3), and the two interlocking parts are directly or indirectly connected to the maxillary and mandibular fixation sources (9). The maxillary joint (2), the mandibular joint (3), and the connector (4) will not separate from each other when an external force of less than a fixed level is applied. Therefore, an intermaxillary fixation force can be applied between the upper and lower jaws.

The maxillary joint (2) and the connector (4), and the mandibular joint (3) and the connector (4) are in an adhering state, and can be separated when an external force of a fixed magnitude or greater is applied. For this reason, when an external force having a fixed strength or greater than the intermaxillary fixation force acts on the counterpart surfaces of the maxillary joint (2) and the connector (4) and the counterpart surfaces of the mandibular joint (3) and the connector (4) in a state in which the intermaxillary fixation releasing device (1) is directly or indirectly connected to the fixation sources (9) of the upper and lower jaws, elastomeric connector (4) deforms, the counterpart surfaces peel away, and the maxillary joint (2), the mandibular joint (3), and the connector (4) separate.

The second aspect has the same basic configuration as the first aspect and in this respect has the same effect as the first aspect. In addition to the configuration of the first aspect, the second aspect is provided with a configuration in which the upper-side support part (22) of the maxillary joint and the lower-side support part (32) of the mandibular joint (3) are embedded in the connector. In other words, when the upper-side support part (22) and the lower-side support part (32) are joined with the connector (4), the maxillary joint (2) and the mandibular joint (3) have the upper-side support part (22) and the lower-side support part (32) embedded in the connector (4), which is in a molten state in the manufacturing process, and subsequent cooling yields a completely joined state with respect to the connector (4). However, the upper-side support part (22) of the maxillary joint (2) and the lower-side support part (32) of the mandibular joint (3) are not completely integrated.

The maxillary joint (2) and the mandibular joint (3) are each embedded in the elastomeric connector (4), the counterpart surfaces of the maxillary joint (2) and the connector (4) adhere to each other, the counterpart surfaces of the mandibular joint (3) and the connector (4) adhere to each other, and a fixed level of adhesive force is exhibited.

The third and fourth aspects have a configuration in which the upper-side support part (22) and the lower-side support part (32) are in contact with each other. Therefore, when the intermaxillary fixation releasing device (1) is mounted and fastened shut with a wire, considerable deformation of the connector, which occurs when the maxillary joint and the mandibular joint thus in mutual contact interfere with each other, can be reduced as the connector continues to flex and deform. Also, when the maxillary joint and the mandibular joint are removed from the connector, the maxillary joint (2) moves upward and the mandibular joint (3) moves downward while the maxillary joint (2) and the mandibular joint (3) are in contact. Therefore, the external force required for separation and the loss expended by the deformation of the elastomer are reduced, and the operation for separating the maxillary joint (2) and the mandibular joint (3) is facilitated.

The fifth aspect has a configuration in which the connector (4) is provided with a connector attaching part (45) on an intraoral surface; the maxillary joint (2) is provided with a maxillary joint attaching part (26) on an upper-side support part (22); the upper-side interlocking part (21) is provided with an insertion hole (25) in the lengthwise direction; a bottom surface 210 of the upper-side interlocking part (21) is the contact surface with the center upper surface of the connector, and an inner surface (220) of the upper-side support part (22) is the contact surface with the intraoral surface (42) of the connector (4); the mandibular joint (3) is provided with a mandibular joint attaching part (36) on the lower-side support part (32); the lower-side interlocking part (31) is provided with and insertion hole (35) in the lengthwise direction; and an upper surface 310 of the lower-side interlocking part (31) is the contact surface with the center lower surface of the connector, and an inner surface (320) of the lower-side support part (32) is the contact surface on the intraoral surface (42) of the connector (4). Accordingly, the connector attaching part (45) of the connector (4) is formed in a molten state and attached to the maxillary joint attaching part (26) and the mandibular joint attaching part (36). In this state, the upper-side interlocking part (21) and the lower-side interlocking part (31) having the insertion holes (25), (35) are disposed protruding in the vertical direction in the center of the core part (46) of the connector (4).

This configuration has the insertion hole (25) of the upper-side interlocking part (21), the insertion hole (35) of the lower-side interlocking part (31), and the connector (4) positioned in substantially the same plane. Therefore, in a state in which the intermaxillary fixation releasing device (1) is mounted and fastened shut with a wire, the device can be made less liable to deform due to the tensile force of the wire. The separation of the maxillary joint (2), the mandibular joint (3), and the elastomeric connector (4) can be facilitated.

In accordance with the sixth aspect, a configuration is provided in which a tongue-shaped holding part (41) is formed at the two ends of the core part (46) of the connector (4). The maxillary joint (2), the mandibular joint (3), and the connector (4) are separated by applying an external force having a fixed strength or greater than the intermaxillary fixation force by grasping and pulling one of the holding parts (41).

In accordance with the seventh and eighth aspects, a display part (44) for displaying characters, drawings, symbols, or the like for instructions on releasing the connector (4) or other information is formed on the outer surface of the connector (4), whereby a person who sees the display part (44) can readily understand that the connector (4) is to be pulled.

In accordance with the first to eighth aspects described above, an intermaxillary fixation releasing device (1) is provided to the practitioner as a ready-made product. Therefore, the labor of the practitioner is reduced, and the device can be used by the practitioner irrespective of their skill and experience. The intermaxillary fixation releasing device (1) can be mounted and adjusted in a short amount of time and the burden on the patient can be reduced. Since the intermaxillary fixation releasing device (1) can be disassembled by finger manipulation, the intermaxillary fixation can be removed without any special tools, even by a person having no knowledge about releasing intermaxillary fixation. Also, a conventional wire is used in the mounted state of the intermaxillary fixation releasing device (1) of the present invention. Therefore, a person who knows only the common intermaxillary fixation removal method can remove the intermaxillary fixation by conventional wire cutting. Accordingly, there is an advantage that a person who is skilled only in the common method for releasing intermaxillary fixation can remove intermaxillary fixation using the conventional method, even without understanding of the removal method of the present invention.

In accordance with the second aspect, the upper-side support part (22) of the maxillary joint and the lower-side support part (32) of the mandibular joint (3) are embedded in the connector in the configuration of the first aspect. In other words, when the upper-side support part (22) and the lower-side support part (32) are joined to the connector (4), the maxillary joint (2) and the mandibular joint (3) have the upper-side support part (22) and the lower-side support part (32) embedded in the connector (4), which is in a molten state in the manufacturing process. Subsequent cooling yields a completely joined state with respect to the connector (4), but the upper-side support part (22) of the maxillary joint (2) and the lower-side support part (32) of the mandibular joint (3) are not completely integrated. The maxillary joint (2) and the mandibular joint (3) are each embedded in the elastomeric connector (4), the counterpart surfaces of the maxillary joint (2) and the connector (4) are set in an adhering state, the counterpart surfaces of the mandibular joint (3) and the connector (4) are set in the adhering state, a fixed level of adhesive force is exhibited, and the intermaxillary fixation and the releasing of the intermaxillary fixation can be optimized.

The third and fourth aspects have a configuration in which the upper-side support part (22) and the lower-side support part (32) are in mutual contact. Therefore, when the intermaxillary fixation releasing device (1) is mounted and fastened shut with a wire, considerable deformation of the connector, which occurs when the maxillary joint and the mandibular joint thus in mutual contact interfere with each other, can be reduced as the connector continues to flex and deform. Also, when the maxillary joint and the mandibular joint are removed from the connector, the maxillary joint (2) moves upward and the mandibular joint (3) moves downward while the maxillary joint (2) and the mandibular joint (3) are in contact. Therefore, the external force required for separation and the loss expended by the deformation of the elastomer are reduced, and the operation for separating the maxillary joint (2) and the mandibular joint (3) is facilitated.

The fifth aspect of the present invention has a configuration in which the connector is provided with a connector attaching part on an intraoral surface; the maxillary joint (2) is provided with a maxillary joint attaching part (26) on an upper-side support part (22); the upper-side interlocking part (21) is provided with an insertion hole (25) in the lengthwise direction; a bottom surface (210) of the upper-side interlocking part (21) is the contact surface with the center upper surface of the connector, and an inner surface (220) of the upper-side support part (22) is the contact surface with the intraoral surface (42) of the connector (4); the mandibular joint (3) is provided with a mandibular joint attaching part (36) on the lower-side support part (32); the lower-side interlocking part (31) is provided with and insertion hole (35) in the lengthwise direction; and an upper surface (310) of the lower-side interlocking part (31) is the contact surface with the center lower surface of the connector, and an inner surface (320) of the lower-side support part (32) is the contact surface on the intraoral surface (42) of the connector (4). Accordingly, the connector attaching part of the connector is formed in a molten state and attached to the maxillary joint attaching part (26) and the mandibular joint attaching part (36). In this state, the upper-side interlocking part (21) and the lower-side interlocking part (31) having the insertion holes (25), (35) are thereby disposed protruding in the vertical direction in the center of the connector. This configuration positions the insertion hole (25), the insertion hole (35), and the connector (4) in substantially the same plane. Therefore, in a state in which the intermaxillary fixation releasing device (1) is mounted and fastened shut with a wire, the device can be made less liable to deform due to the tensile force of the wire. The separation of the maxillary joint (2), the mandibular joint (3), and the elastomeric connector (4) can be facilitated.

In accordance with the sixth aspect, a tongue-shaped holding part (41) is formed on the connector (4). The maxillary joint (2), the mandibular joint (3), and the connector (4) are separated by applying an external force of a fixed level or greater than the intermaxillary fixation force by grasping and pulling one of the holding parts (41).

In accordance with the seventh and eighth aspects, a display part (44) for displaying characters, drawings, symbols, or the like for instructions on releasing the connector (4) or other information is formed on the outer surface of the connector (4), whereby a person who sees the display part (44) can readily understand that the connector (4) is to be pulled.

BRIEF DESCRIPTION OF THE DRAWINGS

FIG. 22(Y) shows the intermaxillary fixation releasing device 1 according to example 3 of the present invention, in an enlarged cross-sectional view showing the convexity in a state of intermediate protruding distance;

FIG. 22(Z) shows the intermaxillary fixation releasing device 1 according to example 3 of the present invention, in an enlarged cross-sectional view showing the convexity in a state of a small protruding distance;

KEY

Figure 1:
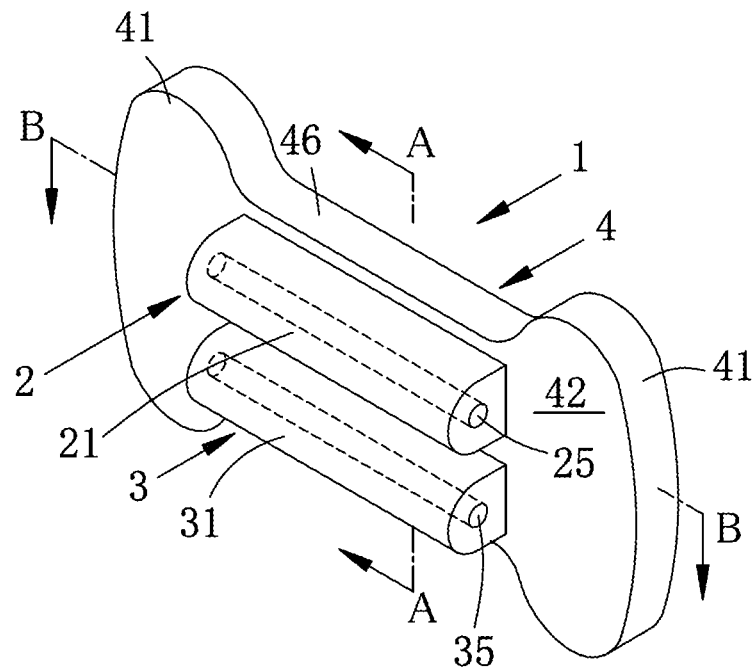
FIG. 1 is an enlarged perspective view of the intermaxillary fixation releasing device 1 according to example 1 of the present invention as seen from the intraoral surface 42 side.

1 Intermaxillary fixation releasing device
2 Maxillary joint
21 Upper-side interlocking part
210 Bottom surface
22 Upper-side support part
220 Inner surface
23 Convexity
23*a* Convexity (lateral)
23*b* Convexity (excluding lateral)
24 Concavity
25 Insertion hole
26 Maxillary joint mounting unit
3 Mandibular joint
31 Lower-side interlocking part
310 Upper surface
32 Lower-side support part
320 Inner surface
33 Convexity
33*a* Convexity (lateral)
33*b* Convexity (excluding lateral)
34 Concavity
35 Insertion hole
36 Mandibular joint attaching part
4 Connector
41 Holding part
42 Intraoral surface
43 Extraoral surface
44 Display part
45 Connector attaching part
46 Core part
5 First casing
51 Holding part for upper-side interlocking part
52 Holding part for lower-side interlocking part
6 Second casing
61 Connector formation cavity
7 Intramaxillary fixation means
71 Metal wire for intermaxillary fixation
72 Hook
8 Ligature wire
9 Fixation source
91 Maxillary row of teeth
92 Mandibular row of teeth

BEST MODE FOR CARRYING OUT THE INVENTION

Specific embodiments (Examples 1 through 3) of the present invention will be described below.

Example 1

First, the configuration of the intermaxillary fixation releasing device 1 according to example 1 will be described.

Figure 2:
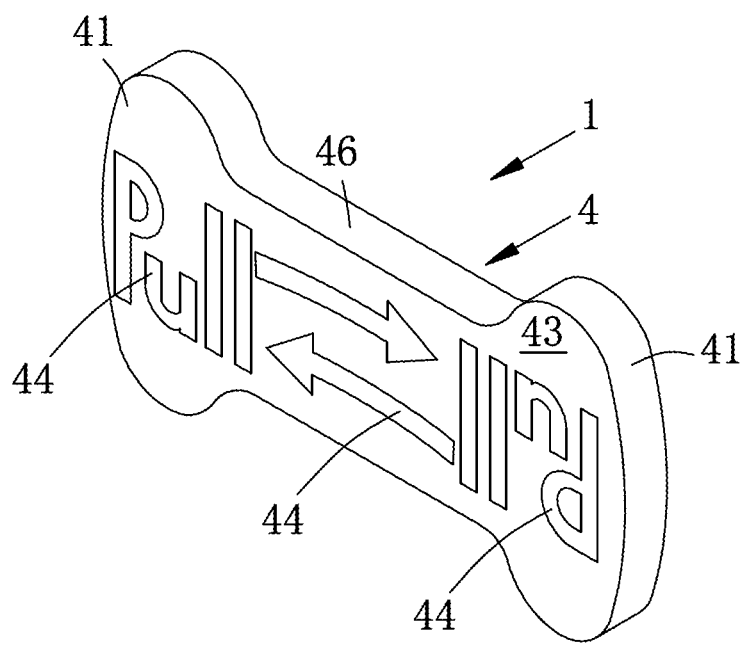
FIG. 2 is an enlarged perspective view of the intermaxillary fixation releasing device 1 according to example 1 of the present invention as seen from the extraoral surface 43 side.
Figure 3:
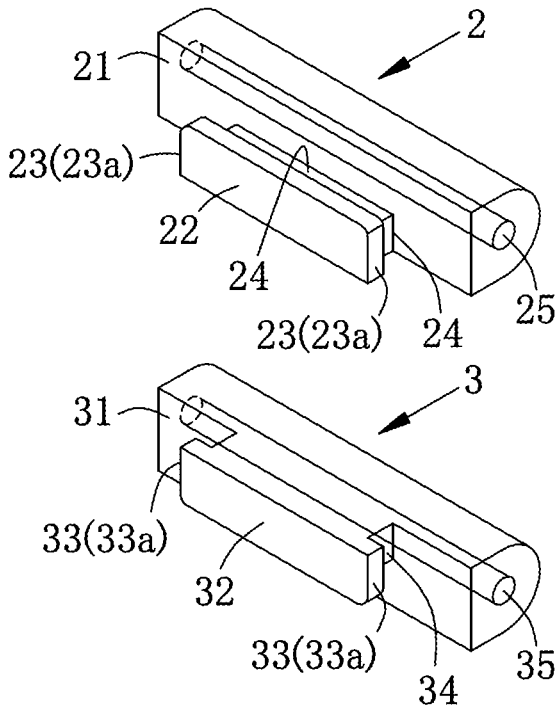
FIG. 3 is an enlarged perspective view of the maxillary joint 2, the mandibular joint 3 and intermaxillary fixation releasing device 1 according to example 1 of the present invention.
Figure 4:
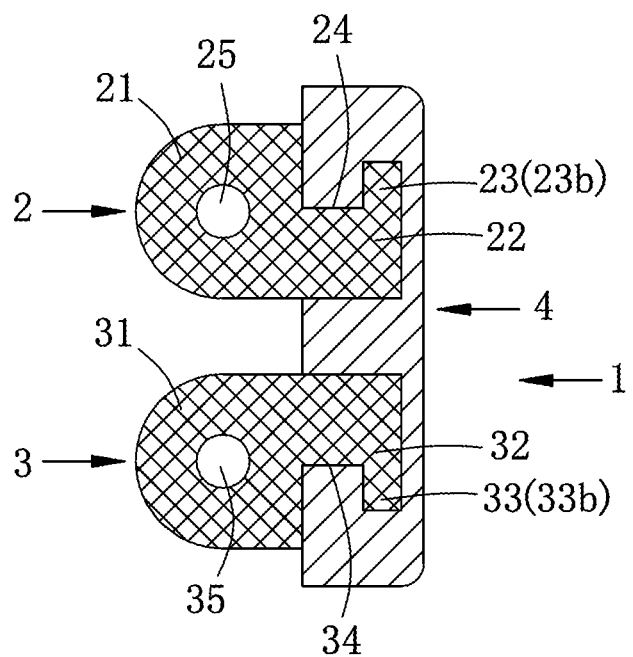
FIG. 4 is an enlarged end surface view sectioned along the line A-A of FIG. 1.
Figure 5:
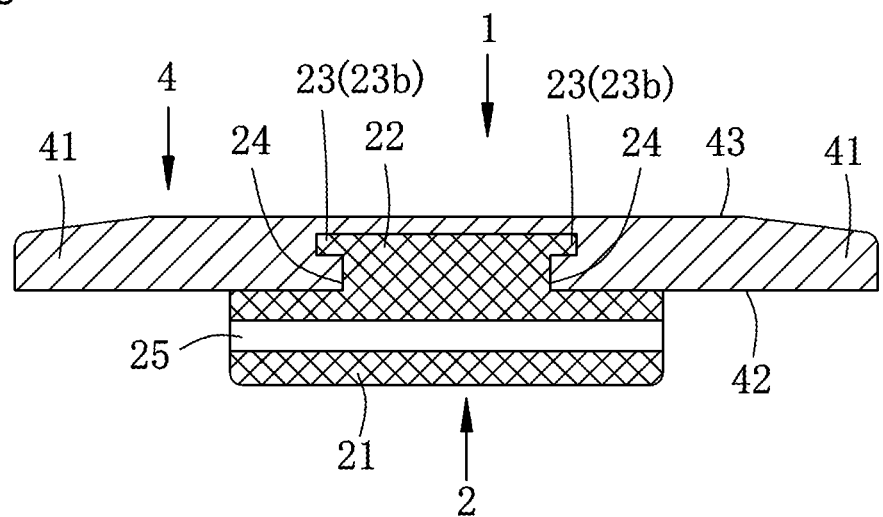
FIG. 5 is an enlarged end surface view sectioned along the line B-B of FIG. 1.
Figure 6:
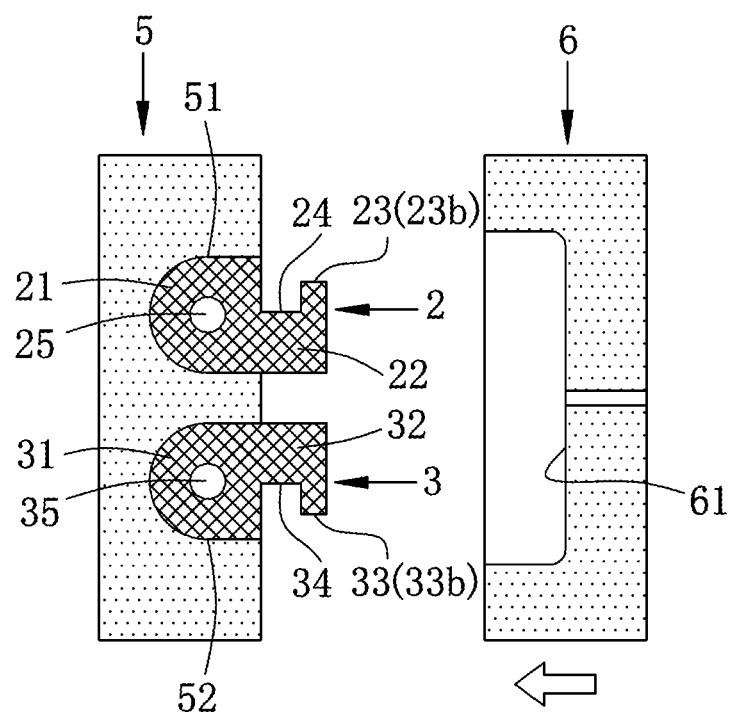
FIG. 6 is a cross-sectional view of the first casing 5 and the second casing 6 in a state in which the maxillary joint 2 and the mandibular joint 3 are held in the first casing 5.
Figure 7:
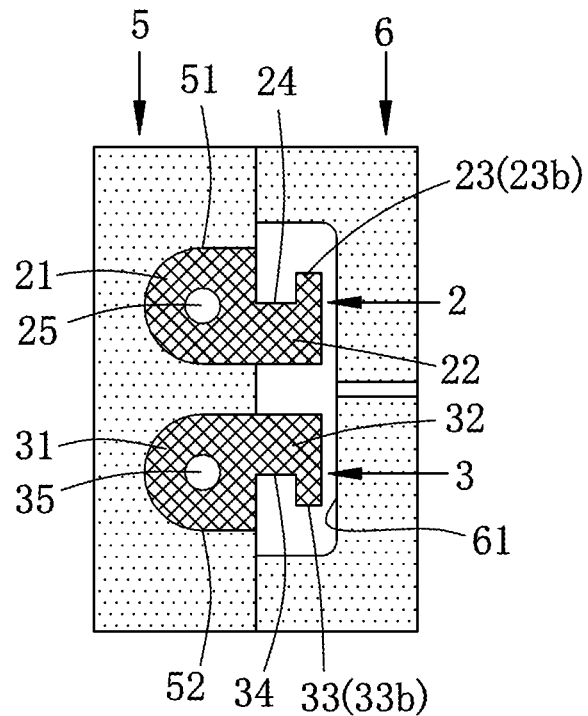
FIG. 7 is a cross-sectional view of the first casing 5 and the second casing 6 in a state in which the second casing 6 and the first casing 5 holding the maxillary joint 2 and the mandibular joint 3 are closed.
Figure 8:
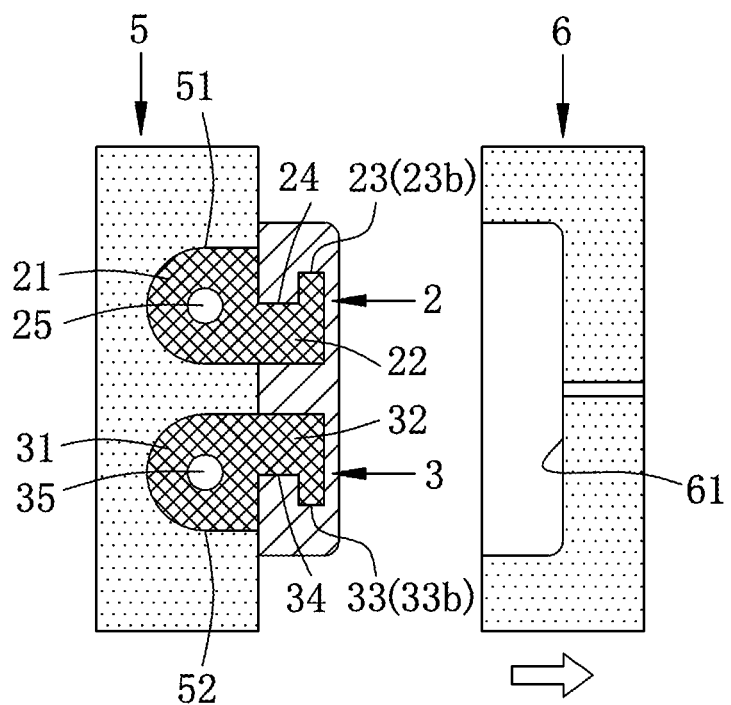
FIG. 8 is a cross-sectional view of the first casing 5 and the second casing 6 in a state in which the first casing 5 and the second casing 6 are closed.
Figure 9:
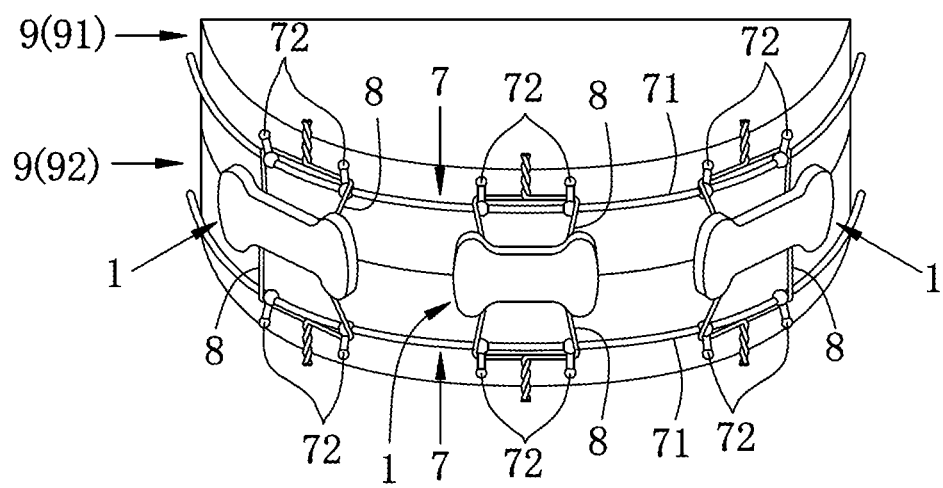
FIG. 9 is a simplified perspective view of the state in which the intermaxillary fixation releasing device 1 is mounted, wherein the intramaxillary fixation means 7 is mounted on the maxillary row of teeth 91 as the fixation source 9 and the mandibular row of teeth 92 as the fixation source 9.
Figure 10:
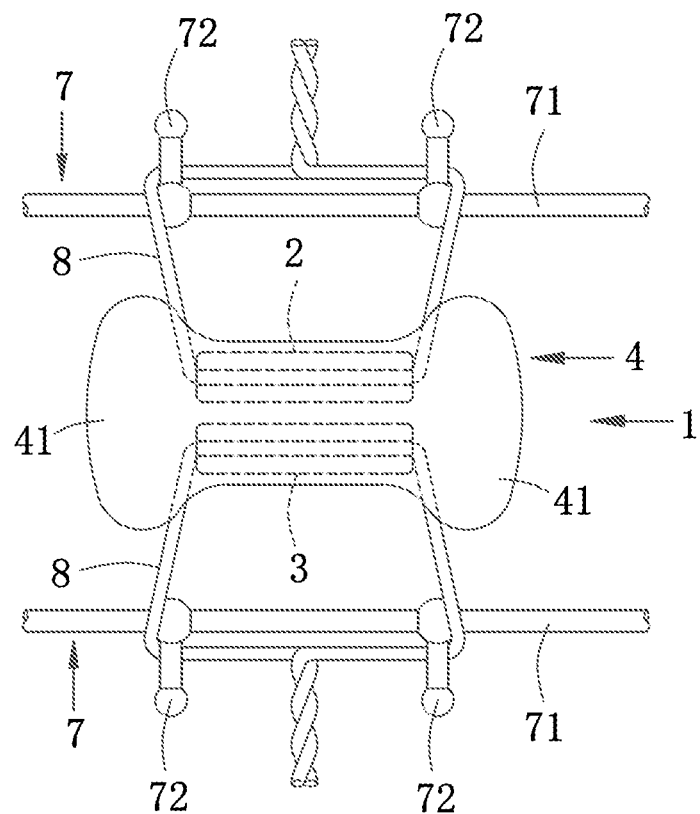
FIG. 10 is an enlarged perspective view of the state in which the intermaxillary fixation releasing device 1 is mounted on the intramaxillary fixation means 7.
Figure 11:
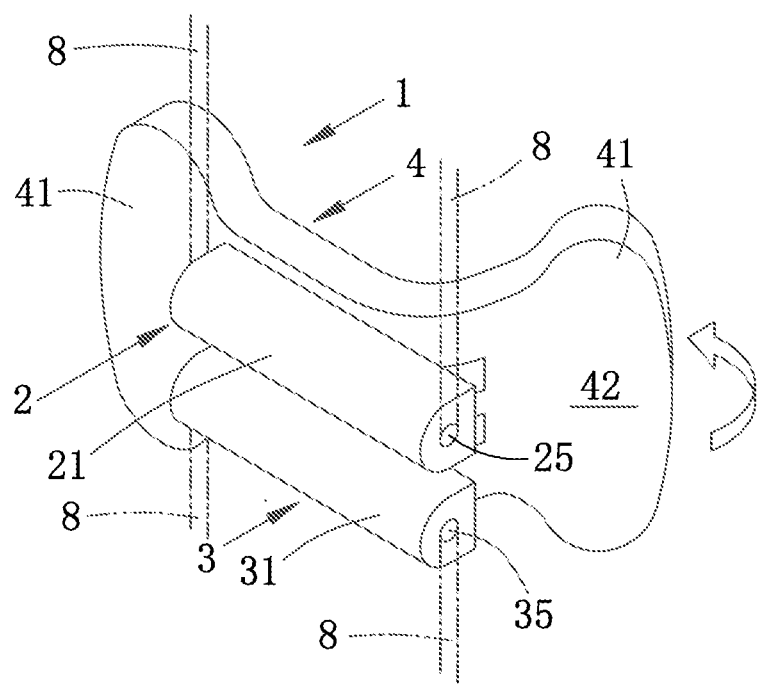
FIG. 11 is an enlarged perspective view as seen from the intraoral surface 42 side, in a state in which the connector 4 has been pulled outward from the mouth in relation to the intermaxillary fixation releasing device 1 mounted on the intramaxillary fixation means 7.
Figure 12:
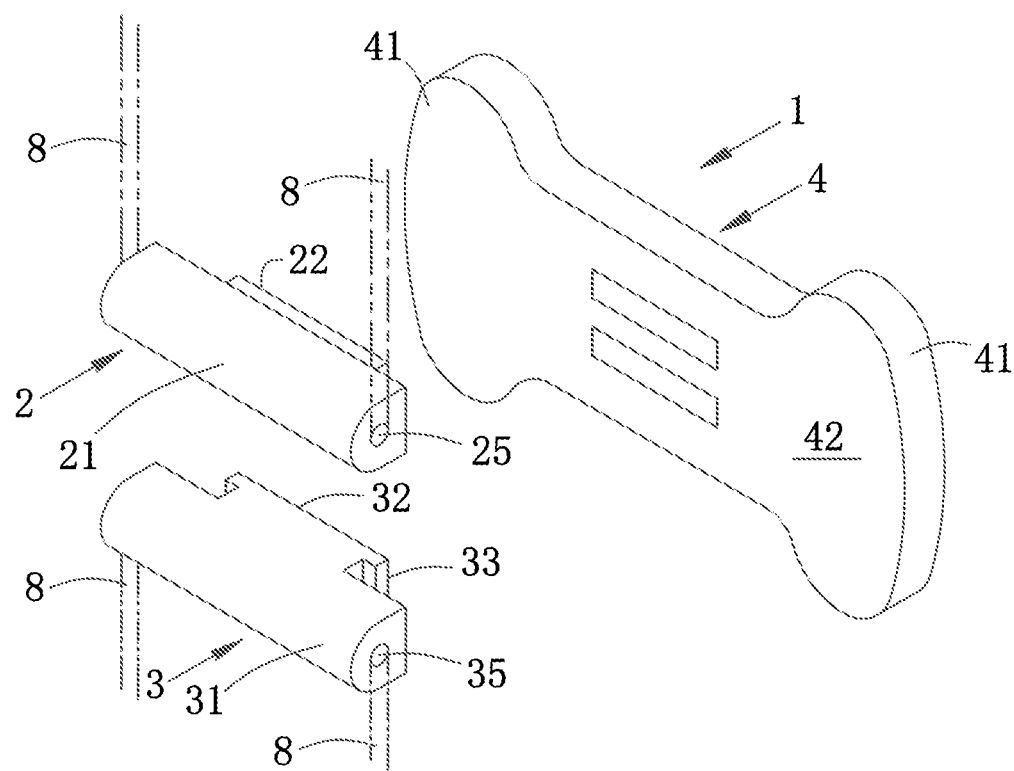
FIG. 12 is an enlarged perspective view as seen from the intraoral surface 42 side, in a state in which the maxillary joint 2, the mandibular joint 3, and the connector 4 are separated from the intermaxillary fixation releasing device 1 and the intermaxillary fixation is removed.

FIG. 1 is an enlarged perspective view of the intermaxillary fixation releasing device 1 according to example 1 of the present invention as seen from the intraoral surface 42. FIG. 2 is an enlarged perspective view of the intermaxillary fixation releasing device 1 according to example 1 of the present invention as seen from the extraoral surface 43. FIG. 3 is an enlarged perspective view of the maxillary joint 2 and the mandibular joint 3 intermaxillary fixation releasing device 1 according to the same example 1. FIG. 4 is an enlarged end surface view sectioned along the line A-A of FIG. 1. FIG. 5 is an enlarged end surface view sectioned along the line B-B of FIG. 1. FIG. 6 is a cross-sectional view of the first casing 5 and the second casing 6 in a state in which the maxillary joint 2 and the mandibular joint 3 are held in the first casing 5. FIG. 7 is a cross-sectional view of the first casing 5 and the second casing 6 in a state in which the second casing 6 and the first casing 5 holding the maxillary joint 2 and the mandibular joint 3 are closed. FIG. 8 is a cross-sectional view of the first casing 5 and the second casing 6 in a state in which the first casing 5 and the second casing 6 are closed. FIG. 9 is a simplified perspective view of the state in which the intermaxillary fixation releasing device 1 is mounted, wherein the intramaxillary fixation means 7 is mounted on the maxillary row of teeth 91 as the fixation source 9 and the mandibular row of teeth 92 as the fixation source 9. FIG. 10 is an enlarged perspective view of the state in which the intermaxillary fixation releasing device 1 is mounted on the intramaxillary fixation means 7. FIG. 11 is an enlarged perspective view as seen from the intraoral surface 42 side, in a state in which the connector 4 has been pulled outward from the mouth in relation to the intermaxillary fixation releasing device 1 mounted on the intramaxillary fixation means 7. FIG. 12 is an enlarged perspective view as seen from the intraoral surface 42 side, in a state in which the maxillary joint 2, the mandibular joint 3, and the connector 4 are separated from the intermaxillary fixation releasing device 1 and the intermaxillary fixation is released.

The intermaxillary fixation releasing device 1 is a disposable intermaxillary fixation releasing device 1, and has a maxillary joint 2, a mandibular joint 3, and a connector 4, as shown in FIG. 1. The maxillary joint 2 and the mandibular joint 3 are secured to the connector 4 by causing a protruding upper-side interlocking part 21 and lower-side interlocking part 31 to protrude. The upper-side interlocking part 21 and the lower-side interlocking part 31 protrude from an intraoral surface 42 of the connector 4. The intraoral surface 42 is the surface that faces the intraoral direction when the intermaxillary fixation releasing device 1 has been mounted between the jaws of a patient. The extraoral surface 43 is the reverse surface of the intraoral surface 42, i.e., the surface that faces the extraoral direction. About three intermaxillary fixation releasing devices 1 are mounted between the upper and lower jaws of the patient. In the present example 1, the length is 210 mm and the height is 10.9 mm.

The maxillary joint 2 according to example 1 is formed from polyethylene. The polyethylene constituting the maxillary joint 2 is a medical grade resin having high hardness (D hardness: about 53 degrees) and is nontoxic and water-resistant. The maxillary joint 2 has an upper-side interlocking part 21 and an upper-side support part 22, as shown in FIG. 3. The upper-side interlocking part 21 is a portion directly or indirectly connected to the maxillary fixation source 9, and, in the present example 1, is indirectly connected to the maxillary fixation source 9. The fixation sources 9 are a maxillary tooth or bone and a mandibular tooth or bone. An insertion hole 25 is formed in the upper-side interlocking part 21. The insertion hole 25 is a hole for inserting a ligature wire 8. The upper-side interlocking part 21 is indirectly connected to the maxillary fixation source 9 via the ligature wire 8. The dimensions of the maxillary joint 2 in terms of length, height, and width are 10.0 mm×2.3 mm×22 mm, and the diameter of the insertion hole 25 is 0.7 mm.

The upper-side support part 22 is a portion connected to the connector 4. The maxillary joint 2 is fixed to the connector 4 by connecting the upper-side support part 22 to the connector 4. The upper-side support part 22 is protrudingly provided to the upper-side interlocking part 21. The fixed end portion of the upper-side support part 22 is the portion in contact with the upper-side interlocking part 21. The fixed end portion of the upper-side support part 22 has a constricted shape that is narrower than the free end portion (see FIGS. 4 and 5). The fixed end portion of the upper-side support part 22 is a constricted portion acting as a concavity 24, and the free end portion of the upper-side support part 22 is a portion thickly formed as a convexity 23. The dimensions of the convexity 23 of the free end portion of the upper-side support part 22 in terms of length, height, and width are 6.0 mm×25 mm×0.5 mm; and those of the concavity 24 of the fixed end portion are 5.0 mm×1.0 mm×0.8 mm.

The mandibular joint 3 is formed from polyethylene in the same manner as the maxillary joint 2. The mandibular joint 3 has a lower-side interlocking part 31 and a lower-side support part 32, as shown in FIG. 3. The configuration of the lower-side interlocking part 31 and the lower-side support part 32 is same as the maxillary joint 2 in FIG. 3 except for being vertically inverted. Therefore, a detailed description is omitted.

The connector 4 according to example 1 is formed from a styrene-based elastomer. The styrene-based elastomer constituting the connector 4 is a medical grade resin having low hardness (A hardness: about 65 degrees) and is nontoxic and water-resistant. The connector 4 holds the upper-side support part 22 of the maxillary joint 2 and the lower-side support part 32 of the mandibular joint 3, as shown in FIGS. 4 and 5.

Inside the connector 4, the styrene-based elastomer of the connector 4 covers the convexities 23, 33 of the upper-side support part 22 and the lower-side support part 32, and the styrene-based elastomer of the connector 4 fills the concavities 24, 34 of the upper-side support part 22 and the lower-side support part 32. The maxillary joint 2 and the mandibular joint 3 are thereby fixed to the connector 4. The connector 4 is provided to the maxillary joint 2 and the mandibular joint 3. Therefore, the maxillary joint 2 and the mandibular joint 3 are joined by the connector 4.

The two ends of the connector 4 are free ends, as shown in FIG. 2. A holding part 41 is formed at the two ends of the connector 4. The holding part 41 is a portion by which the connector 4 is pulled with the fingers and separated from the maxillary joint 2 and the mandibular joint 3. The holding part 41 is of sufficient size to allow grasping by the fingers.

The extraoral surface 43 of the connector 4 has "PULL" and an arrow indicating the direction for pulling displayed on the holding part 41 as a display part 44, on which are displayed characters, drawings, symbols, or the like for instructions on releasing intermaxillary fixation or other information. In the present example 1, the display is also provided upside down, and the display of "PULL" and the arrow can always be understood regardless of the vertical orientation of the intermaxillary fixation releasing device 1. The dimensions of the connector 4 are a length of 210 mm, a height at the holding part 41 of 10.9 mm, a height at the center part of 6.6 mm, and a width of 1.7 mm.

The method for manufacturing the intermaxillary fixation releasing device 1 in the present example 1 will now be described. The manufacturing method is composed of a first step and a second step. In the first step, first, the maxillary joint 2 and mandibular joint 3 described above are formed from a polyethylene resin using injection molding means.

Next, the maxillary joint 2 and the mandibular joint 3 are fixed to the connector 4 in the second step. First, the maxillary joint 2 and the mandibular joint 3 are held in the first casing 5, as shown in FIG. 6. Formed on the first casing 5 are a holding part for the upper-side interlocking part 51 that corresponds to the shape of the upper-side interlocking part 21, and a holding part for the lower-side interlocking part 52 that corresponds to the shape of the lower-side interlocking part 31. The upper-side interlocking part 21 is held by the holding part for the upper-side interlocking part 51 and the lower-side interlocking part 31 is held by the holding part for the lower-side interlocking part 52. The upper-side support part 22 and the lower-side support part 32 are set in a state of being exposed from the first casing 5. The maxillary joint 2 and the mandibular joint 3 are set in parallel and held at the same intervals as the intermaxillary fixation releasing device 1.

Next, the second casing 6 and the first casing 5 holding the maxillary joint 2 and the mandibular joint 3 are closed, as shown in FIG. 7. A connector formation cavity 61 that corresponds to the shape of the connector 4 in the present embodiment is formed in the second casing 6. The upper-side support part 22 and the lower-side support part 32, which are a portion of the maxillary joint 2 and the mandibular joint 3, are exposed in the connector formation cavity 61.

A styrene-based elastomer is injected into the connector formation cavity 61 in the state in which the first casing 5 and the second casing 6 are closed. The molten styrene-based elastomer makes contact with the surface of the maxillary joint 2 and the mandibular joint 3 exposed in the connector formation cavity 61. The styrene-based elastomer covers the convexities 23, 33 of the upper-side support part 22 and the lower-side support part 32, and fills the concavities 24, 34 of the upper-side support part 22 and the lower-side support part 32. The molten styrene-based elastomer is cooled, whereupon the connector 4 is formed and the maxillary joint 2 and the mandibular joint 3 are fixed to the connector 4. The connector 4 is provided to the maxillary joint 2 and the mandibular joint 3. Therefore, the maxillary joint 2 and the mandibular joint 3 are joined by the connector 4. The first casing 5 and the second casing 6 are opened to obtain the intermaxillary fixation releasing device 1, as shown in FIG. 8.

As described above, in the intermaxillary fixation releasing device 1 according to example 1, the molten styrene-based elastomer makes contact with the upper-side support part 22 and the lower-side support part 32, which are a portion of the maxillary joint 2 and the mandibular joint 3 formed from polyethylene, and a connector 4 is formed, thereby fixing the maxillary joint 2 and the connector 4 as well as the mandibular joint 3 and the connector 4. However, the polyethylene and the styrene-based elastomer do not fuse to each other, as shown in FIGS. 4 and 8.

Therefore, the maxillary joint 2, the mandibular joint 3, and the connector 4 are not completely integrated. The counterpart surfaces of the upper-side support part 22 and the connector 4, and the counterpart surfaces of the lower-side support part 32 and the connector 4 are in close contact with each other, and the adhesive force having a fixed strength is exhibited.

The styrene-based elastomer of the connector 4 covers the convexity 23 of the upper-side support part 22 and the lower-side support part 32, and fills the concavity 24 of the upper-side support part 22 and the lower-side support part 32. Therefore, the maxillary joint 2, the mandibular joint 3, and the connector 4 are interlocked in a hook-shape in the convexity 23 and the concavity 24. When an external force acts on the maxillary joint 2 and the mandibular joint 3 so as to separate the two joints from the connector 4, the portion interlocked in a hook-shape exerts an interlocking force against the external force and does not separate. In the presence of an external force of a fixed or greater level, the portion interlocked in a hook-shape yields to the external force, and deforms and stretches until a state in which the interlocking force does not operate is reached.

Accordingly, the adhesive force and the interlocking force are exerted by the maxillary joint 2, the mandibular joint 3, and the connector 4, whereby the intermaxillary fixation releasing device 1 of the present example 1 can support a tensile strength of about 100 N against an equal tensile strength that pulls the maxillary joint 2 and the mandibular joint 3 in the vertical direction.

Next, the procedure for mounting the intermaxillary fixation releasing device 1 of the present example 1 between the upper and lower jaws of a patient will be described. The intermaxillary fixation releasing device 1 of the present example 1 is mounted between the upper and lower jaws via a ligature wire 8; i.e., is indirectly connected to the upper and lower fixation sources 9. Accordingly, the intramaxillary fixation means 7 is mounted on the maxillary and mandibular fixation sources 9 of the patient. In the case that the teeth are used as the fixation source 9, an "intermaxillary fixation splint" or an "orthodontic bracket" can be used as the intramaxillary fixation means 7. The "intermaxillary fixation splint" is means for binding a metal wire for intramaxillary fixation 71, which has a hook 72, to the maxillary and mandibular rows of teeth using a wire. This method is mainly used following corrective surgery for jawbone fracture. The "orthodontic bracket" is means in which an orthodontic bracket is mounted on the maxillary and mandibular rows of teeth, and a metal wire for intramaxillary fixation 71 having a hook 72 is mounted on the maxillary and mandibular brackets. This method is mainly used following orthodontic surgery. When the teeth are not settled or at other times when the teeth are not healthy and cannot be used as a fixation source 9, the jawbone is used as the fixation source 9. In this case, a "bone screw" can be used as the intramaxillary fixation means 7. The "bone screw" is means for embedding a screw in the maxillary and mandibular bones.

The intramaxillary fixation means 7 is mounted on the upper and lower jaws, as shown in FIG. 9. The intramaxillary fixation means 7 is mounted on the buccal side (outer side) of the teeth or bone. In the present example 1, the metal wire for intermaxillary fixation 71 is mounted on the buccal side of the maxillary row of teeth 91 as a fixation source 9 and the buccal side of the mandibular row of teeth 92 as a fixation source 9. The hook 72 is provided to the location in which the intermaxillary fixation releasing device 1 is mounted. The hook 72 is a portion with which the ligature wire 8 is interlocked. The hook 72 is disposed on the metal wire for intermaxillary fixation 71. The intermaxillary fixation releasing device 1 is mounted in the location in which an intermaxillary fixation force must be exerted, and as an example in the present example 1, the intermaxillary fixation releasing device 1 is mounted on the labial and buccal sides of the teeth: a single location on the front teeth, and a single location each on the two sides of the posterior teeth for a total of three locations. Two hooks 72 constituting a pair are provided to the upper and lower jaws as a set of hooks 72. The set of hooks 72 are provided to a single location of the front teeth, and to a single location each on the two sides of the posterior teeth for a total of three locations.

Next, the ligature wire 8 is connected to the intermaxillary fixation releasing device 1, as shown in FIG. 10. The ligature wire 8 connects the intermaxillary fixation releasing device 1 and the intramaxillary fixation means 7 of the upper jaw, and connects the intermaxillary fixation releasing device 1 and the intramaxillary fixation means 7 of the lower jaw. The maxillary joint 2 is connected to the intramaxillary fixation means 7 of the upper jaw via the ligature wire 8, and the mandibular joint 3 is connected to the intramaxillary fixation means 7 of the lower jaw via the ligature wire 8. The ligature wire 8 for maxillary ligation is inserted into the insertion hole 25 of the maxillary joint 2, and the ligature wire 8 for mandibular ligation is inserted into the insertion hole 35 of the mandibular joint 3. The ligature wire 8 is joined and looped by being inserted through the insertion holes 25, 35 and twisted, or by using other means. The looped ligature wire 8 is interlocked with the hook 72.

Next, an intermaxillary fixation force is applied between the upper and lower jaws. The intermaxillary fixation force is applied by adjusting the length of the ligature wire 8. The twisted ends in which the two ends of the ligature wire 8 are joined are further twisted, as shown in FIG. 10. The looped portion formed from the ligature wire 8 is shortened by twisting the ligature wire 8. The tensile force applied to the ligature wire 8 by shortening the looped portion, and the required intermaxillary fixation force is applied. The point related to the adjustment of the intermaxillary fixation force by twisting the ligature wire 8 is the same as that of conventional intermaxillary fixation means, and the magnitude of the intermaxillary fixation force is adjusted by increasing or reducing the twisting. The length of the ligature wire 8 is adjusted so that the intermaxillary fixation releasing device 1 is mounted in a substantially intermediate position between the upper and lower jaws (see FIG. 9).

The procedure that is used when the intermaxillary fixation is removed will now be described. The removal procedure is very simple. The intermaxillary fixation releasing device 1 is mounted substantially in the center part between the upper and lower jaws and can be extraorally confirmed from the slightly opened lips of the patient, as shown in FIG. 9. The holding part 41 formed on the connector 4 is grasped by the fingers and pulled outward from the mouth, as shown in FIG. 11. At this point, the force applied by finger manipulation acts as a force for peeling away the counterpart surfaces of the maxillary joint 2 and the connector 4 as well as the mandibular joint 3 and the connector 4. When the counterpart surfaces are peeled away, the maxillary joint 2, the mandibular joint 3, and the connector 4 are separated from each other, and the intermaxillary fixation is removed, as shown in FIG. 12.

The reason that the counterpart surfaces are peeled away by pulling the holding part 41 by finger manipulation is that, first, the force that peels the counterpart surfaces away is locally applied at the end part near the holding part 41. The force locally applied to the end part causes the counterpart surfaces to partially peel away. When the holding part 41 is pulled further, the counterpart surfaces sequentially peel away from the end part near the holding part 41 toward the center part, and then to the end parts of the opposite sides. Since the connector 4 is formed from a soft resin, the connector 4 deforms and the upper-side support part 22 and the lower-side support part 32 are removed. When all the counterpart surfaces are peeled away, the intermaxillary fixation releasing device 1 is disassembled, the maxillary joint 2 and the mandibular joint 3 are separated, and the intermaxillary fixation is thereby removed. For example, the maxillary joint 2 and the mandibular joint 3 become separated and the intermaxillary fixation is removed even when all the counterpart surfaces do not separate, such as in the case that the maxillary joint 2 and the connector 4 are separated, and the mandibular joint 3 and the connector 4 are not completely separated.

Example 2

Figure 13:
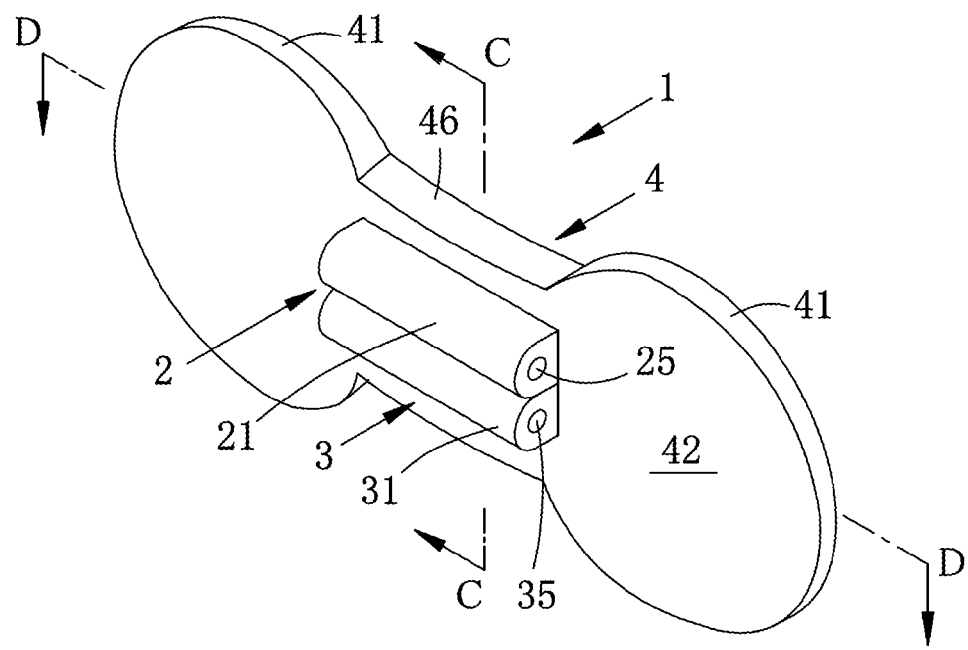
FIG. 13 is an enlarged perspective view of the intermaxillary fixation releasing device 1 according to the second example of the present invention as seen from the intraoral surface 42 side.
Figure 14:
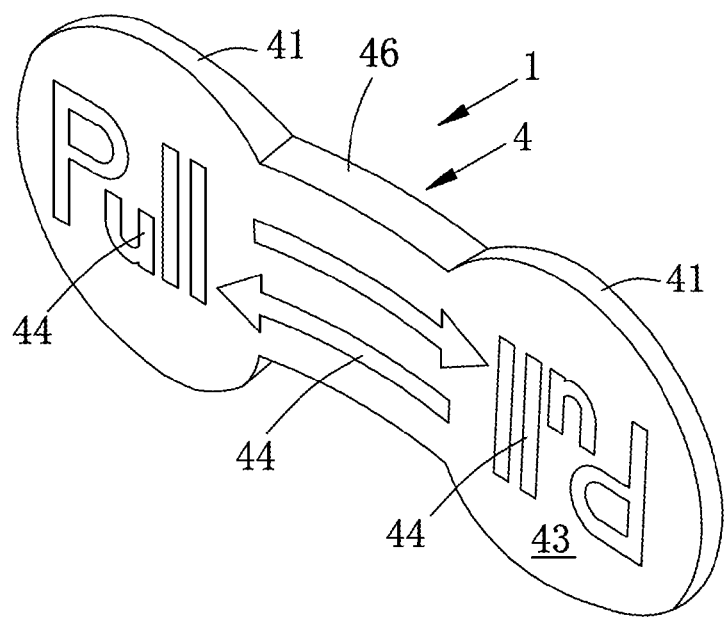
FIG. 14 is an enlarged perspective view of the intermaxillary fixation releasing device 1 according to example 2 of the present invention as seen from the extraoral surface 43 side.
Figure 15:
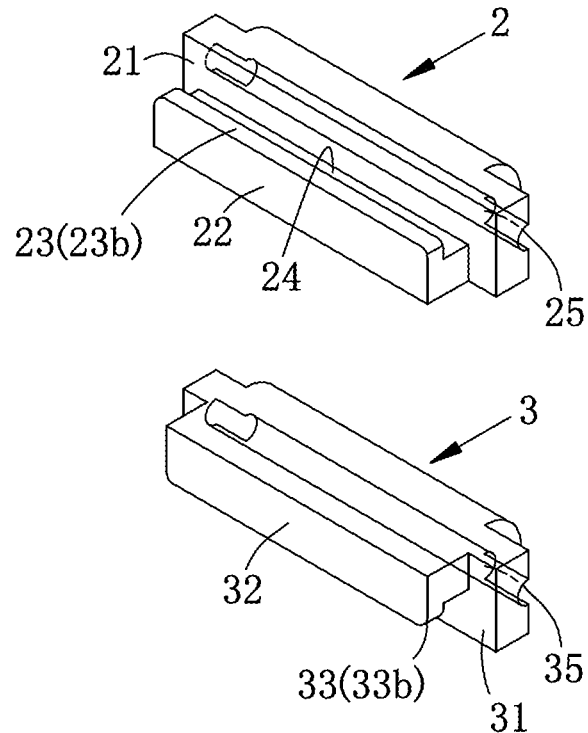
FIG. 15 is an enlarged perspective view of the maxillary joint 2 and the mandibular joint 3 of the intermaxillary fixation releasing device 1 according to example 2 of the present invention.
Figure 16:
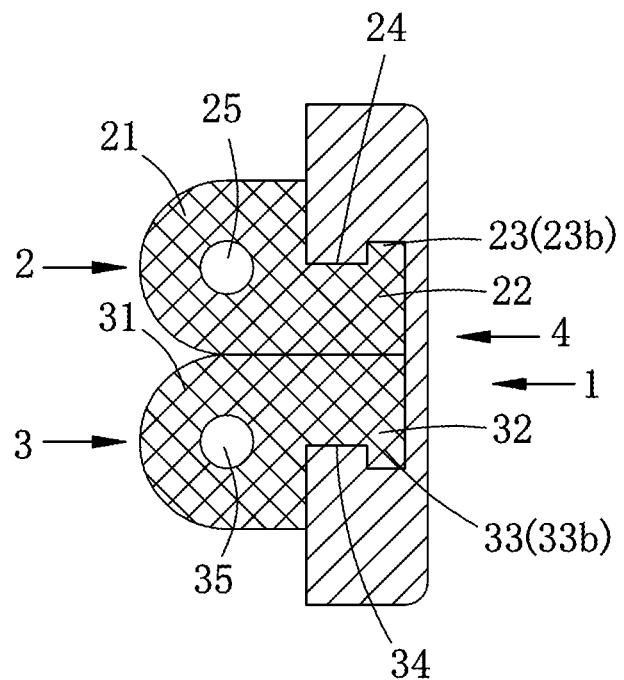
FIG. 16 is an enlarged end surface view of the intermaxillary fixation releasing device 1 according to example 2 of the present invention, as viewed in direction C-C.
Figure 17:
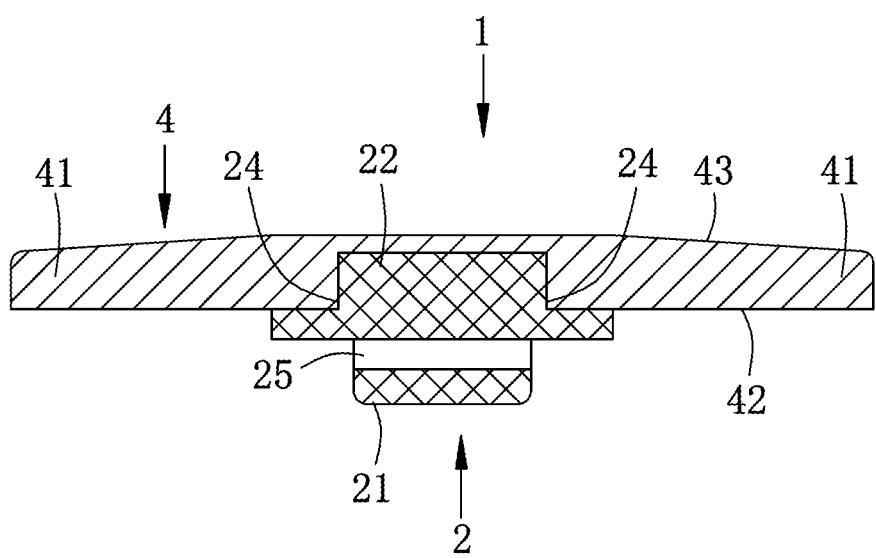
FIG. 17 is an enlarged end surface view of the intermaxillary fixation releasing device 1 according to example 2 of the present invention, as viewed in direction D-D.
Figure 18X:
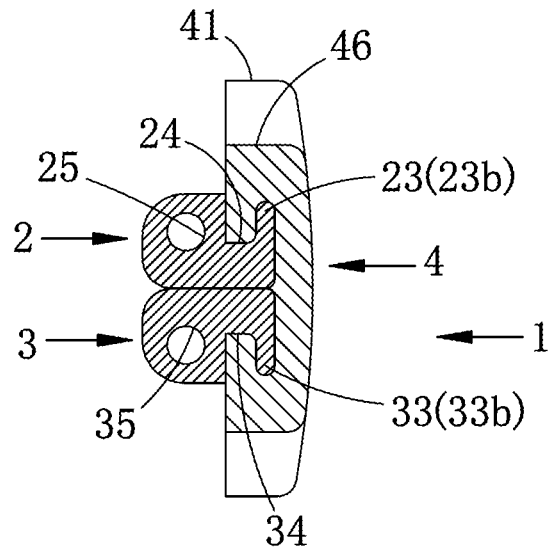
FIG. 18(X) is a cross-sectional view according to example 2 of the present invention, as viewed in direction C-C, showing the convexity in a state of a large protruding distance.
Figure 18Y:
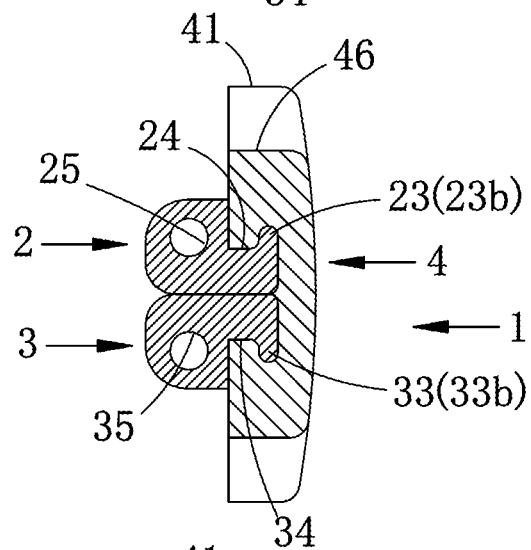
FIG. 18(Y) is a cross-sectional view according to example 2 of the present invention, as viewed in direction C-C, showing a state of an intermediate protruding distance.
Figure 18Z:
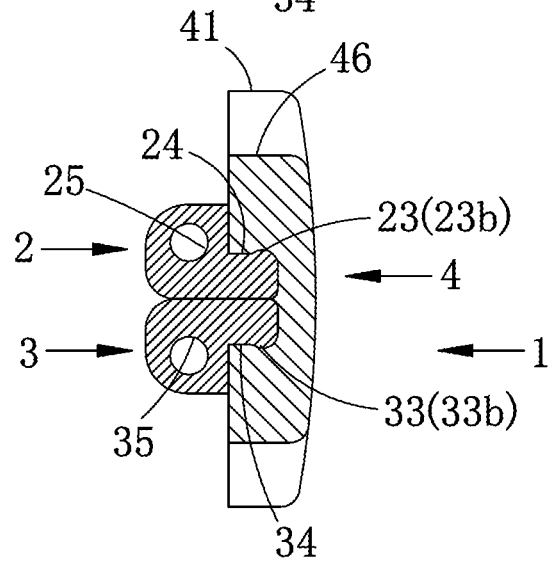
FIG. 18(Z) is a cross-sectional view according to example 2 of the present invention, as viewed in direction C-C, showing a state of a small protruding distance.

The intermaxillary fixation releasing device 1 according to example 2 of the present invention will now be described. FIG. 13 is an enlarged perspective view of the intermaxillary fixation releasing device 1 according to the second example of the present invention as seen from the intraoral surface 42 side. FIG. 14 is an enlarged perspective view of the intermaxillary fixation releasing device 1 according to example 2 of the present invention as seen from the extraoral surface 43 side. FIG. 15 is an enlarged perspective view of the maxillary joint 2 and the mandibular joint 3 of the intermaxillary fixation releasing device 1 according to example 2 of the present invention. FIG. 16 is an enlarged end surface view sectioned along line C-C of FIG. 13. FIG. 17 is an enlarged end surface view sectioned along line D-D of FIG. 13. FIG. 18 is a C-C cross-sectional view in which (X) shows the convexity in a state of a large protruding distance, (Y) shows a state of an intermediate protruding distance, and (Z) shows a state of a small protruding distance.

The configuration is the same as the intermaxillary fixation releasing device according to example 1 described above, wherein the intermaxillary fixation releasing device 1 according to example 2 has a maxillary joint 2, a mandibular joint 3, and a connector 4; the maxillary joint 2 and the mandibular joint 3 cause the upper-side interlocking part 21 and the lower-side interlocking part 31, respectively, to protrude; and the upper-side support part 22 and the lower-side support part 32 are embedded and fixed.

The intermaxillary fixation releasing device 1 according to the present example 2 modifies the shape of the maxillary joint 2 and the mandibular joint 3, and modifies the distance between the maxillary joint 2 and the mandibular joint 3 to bring the maxillary joint 2 and the mandibular joint 3 into contact, whereby the separating operation is facilitated.

The size of the intermaxillary fixation releasing device 1 according to the present example 2 in terms of length and height is 30.0 mm×11.0 mm. The sizes of the maxillary joint 2 and the mandibular joint 3 are in terms of length, height, and width is 35.0 mm×25.0 mm×10 mm, and the diameter dimension of the insertion hole is 1.0 mm. The size of the connector 4 is a length of 30.0 mm, a height at the holding part 41 of 11.0 mm, a height at the center part of 7.6 mm, and a width of 1.7 mm.

The maxillary joint 2 in the intermaxillary fixation releasing device according to the present example 2 has a configuration in which the width of the cylindrical part in which the insertion hole 25 is provided in the upper-side interlocking part 21 is set to be less that the entire width of the upper-side interlocking part 21. The width of the upper-side support part 22 is less than the entire width of the upper-side interlocking part 21, the laterally protruding convexity disclosed in example 1 is not formed on the side part of the upper-side support part 22, and the width of the upper-side support part 22 as such is constant.

The width of the upper-side support part 22 is constant and the concavity 24 of the fixed end portion has a height dimension (i.e., the protruding distance of the convexity 23b) that is set to be less than the height dimension (the protruding distance of the convexity 23b) of the concavity 24 according to example 1.

The mandibular joint 3 is the same shape as the maxillary joint 2 according to the present example 2 and can be used by inverting the joint in the vertical direction. Therefore, the width of the lower-side support part 32 is constant, and the concavity 34 of the fixed end portion has a height dimension (i.e., the protruding distance of the convexity 33b) that is set to be less than the height dimension (the protruding distance of the convexity 33b) of the concavity 34 according to example 1.

The force required for separating the maxillary joint 2, the mandibular joint 3, and the connector 4 from each other can be adjusted by adjusting the height dimension of the concavities 24, 34, as shown in FIG. 18.

In such a configuration, when the holding part 41 is pulled and the maxillary joint 2, the mandibular joint 3, and the connector 4 are separated from each other, the separation can be very readily carried out because the force for peeling away the connector 4 is concentrated on the narrow cylindrical portion.

Example 3

Figure 19:
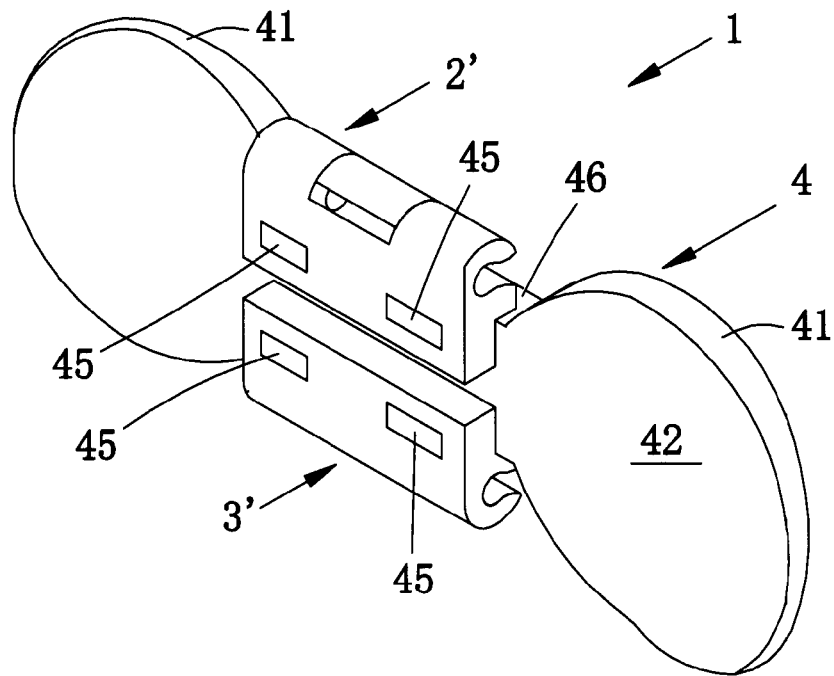
FIG. 19 is an enlarged perspective view as seen from the intraoral surface 42 side of the intermaxillary fixation releasing device 1 according to example 3 of the present invention.
Figure 20:
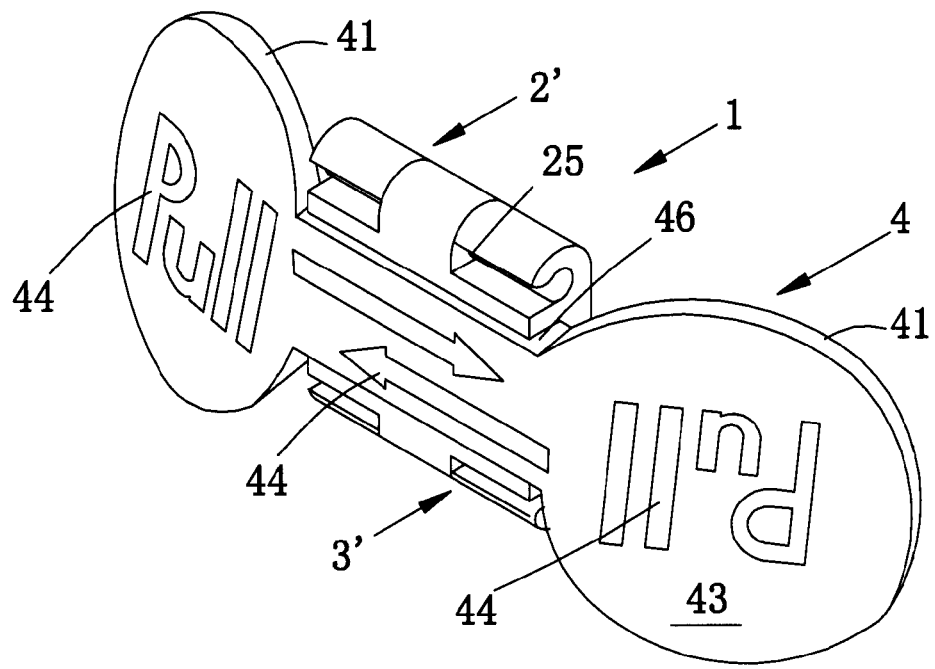
FIG. 20 is an enlarged perspective view as seen from the extraoral surface 43 side of the intermaxillary fixation releasing device 1 according to example 3 of the present invention.
Figure 21X:
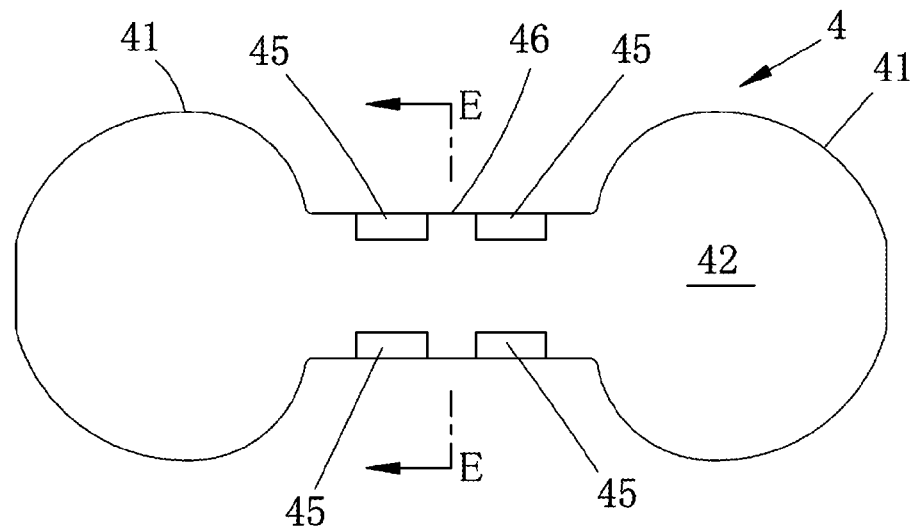
FIG. 21(X) is an enlarged front view as viewed in direction E-E, of the connector 4 (intraoral surface side) according to example 3 of the present invention.
Figure 21Y:
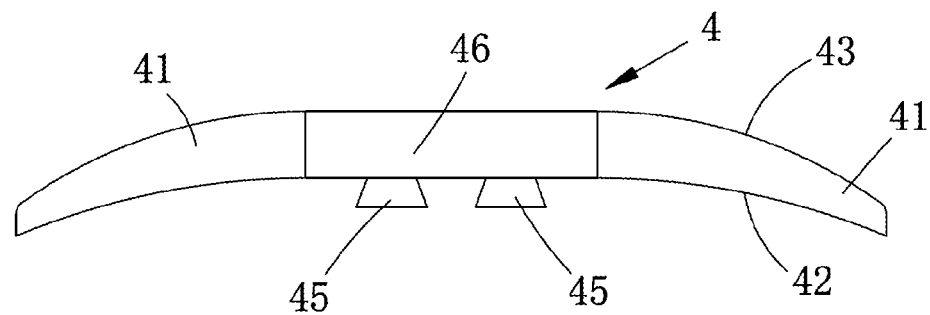
FIG. 21(Y) is an enlarged plan view, as viewed in direction E-E, of the connector 4 (intraoral surface side) according to example 3 of the present invention.
Figure 21Z:
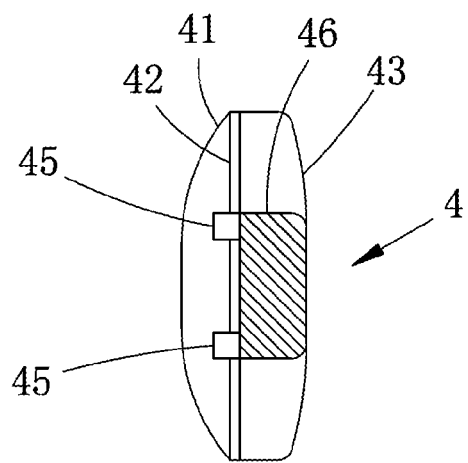
FIG. 21(Z) is an enlarged cross-sectional view as viewed in direction E-E, of the connector 4 (intraoral surface side) according to example 3 of the present invention.
Figure 22X:
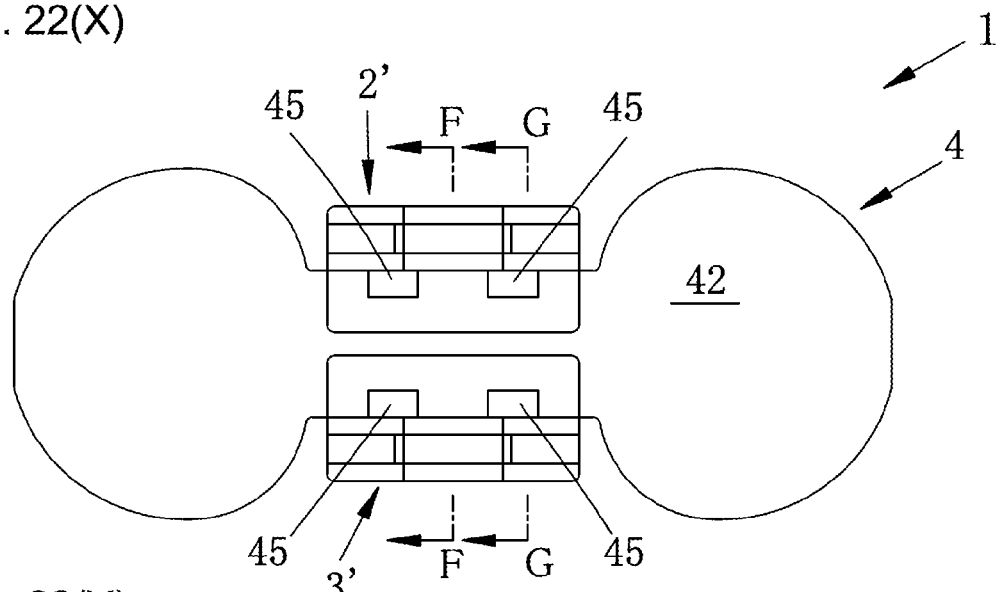
FIG. 22(X) is an enlarged front view of the intermaxillary fixation releasing device 1 according to example 3 of the present invention.

The intermaxillary fixation releasing device 1 according to example 3 of the present invention will now be described. FIG. 19 is an enlarged perspective view as seen from the intraoral surface 42 side of the intermaxillary fixation releasing device 1 according to example 3 of the present invention. FIG. 20 is an enlarged perspective view as seen from the extraoral surface 43 side of the intermaxillary fixation releasing device 1 according to example 3 of the present invention. FIG. 21 is an enlarged front view (X), an enlarged plan view (Y), and an E-E enlarged cross-sectional view (Z), of the connector 4 (intraoral surface) according to present example 3. FIG. 22 is an enlarged front view (X), an enlarged cross-sectional view (Y) as viewed in direction F-F and an enlarged cross-sectional view (Z) as viewed in direction G-G, of the intermaxillary fixation releasing device 1 according to the present example 3. FIG. 23 shows the intermaxillary fixation releasing device 1 according to example 3 of the present invention, wherein (X) is an enlarged cross-sectional view showing the convexity in a state of a large protruding distance, (Y) is an enlarged cross-sectional view showing the convexity in a state of intermediate protruding distance, and (Z) is an enlarged cross-sectional view showing the convexity in a state of a state of a small protruding distance.

The intermaxillary fixation releasing device 1 according to example 3 of the present invention has a configuration that is different from examples 1 and 2 in relation to the configuration of the connector 4, the configuration of the maxillary joint 2' and the mandibular joint 3', the relative arrangements thereof, and the like, as shown in FIGS. 19 and 20. In other words, in examples 1 and 2, the upper-side interlocking part 21' and the lower-side interlocking part 31' protrude to the intraoral surface 42 side in the connector 4, but protrude to the upper and lower surfaces of the core part 46 of the connector 4 in the present example 3.

In other words, the connector 4 according to the present example 3 has a configuration in which the connector attaching part 45a is provided to the intraoral surface 42 in the core part 46, as shown in FIGS. 21 (X), (Y), and (Z). The maxillary joint 2' has a hole-shaped maxillary joint attaching part 26 having a rectangular profile as viewed from the front provided to the upper-side support part 22, and the upper-side interlocking part 21' is provided with an insertion hole 25 in the lengthwise direction. The mandibular joint 3 has a mandibular joint attaching part 36 provided to the lower-side support part 32', and the lower-side interlocking part 31' is provided with an insertion hole 35 in the lengthwise direction. The maxillary joint 2' and the mandibular joint 3' are components having the same shape and are disposed facing each other in the same manner as the other examples 1 and 2.

Figure 22Y:
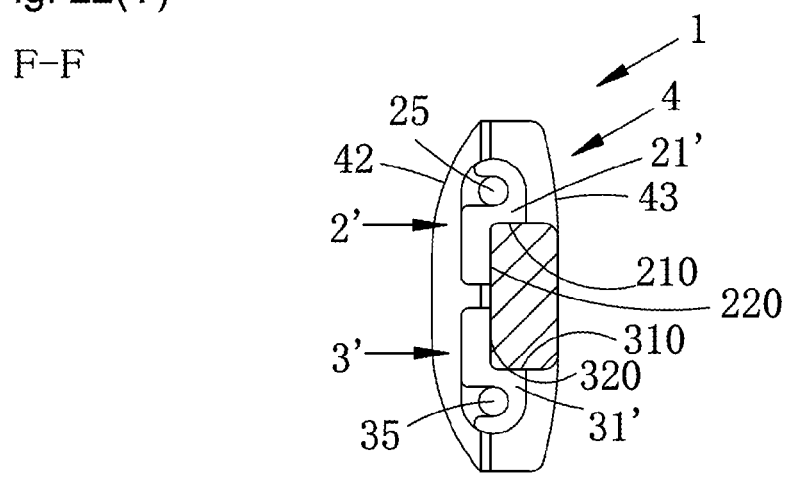
FIG. 22(Y) is an enlarged cross-sectional view, as viewed in direction F-F of the intermaxillary fixation releasing device 1 according to example 3 of the present invention.
Figure 22Z:
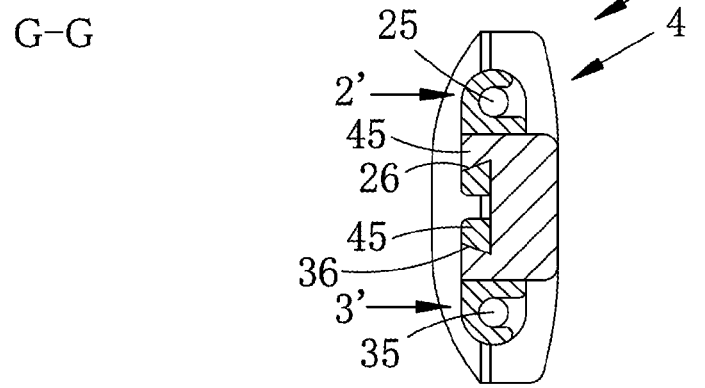
FIG. 22(Z) is an enlarged cross-sectional view, as viewed in direction G-G, of the intermaxillary fixation releasing device 1 according to example 3 of the present invention.
Figure 23X:
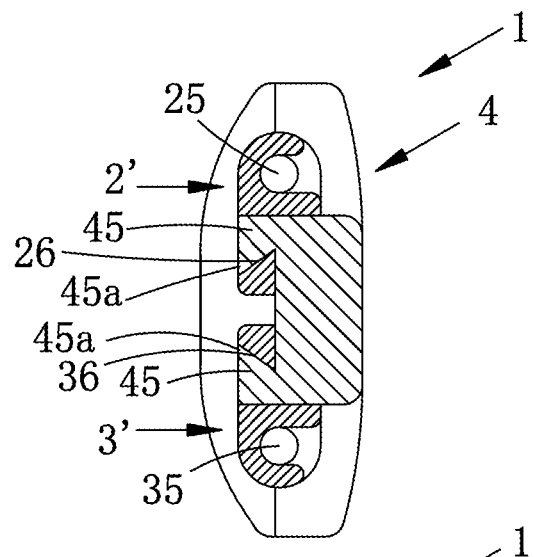
FIG. 23(X) shows the intermaxillary fixation releasing device 1 according to example 3 of the present invention, in an enlarged cross-sectional view showing the convexity in a state of a large protruding distance.
Figure 23Y:
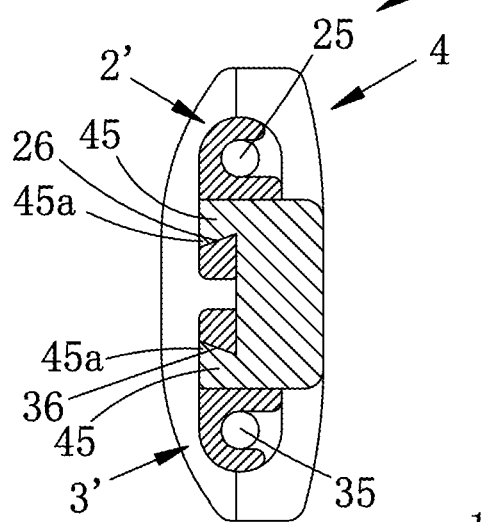
Figure 23Z:
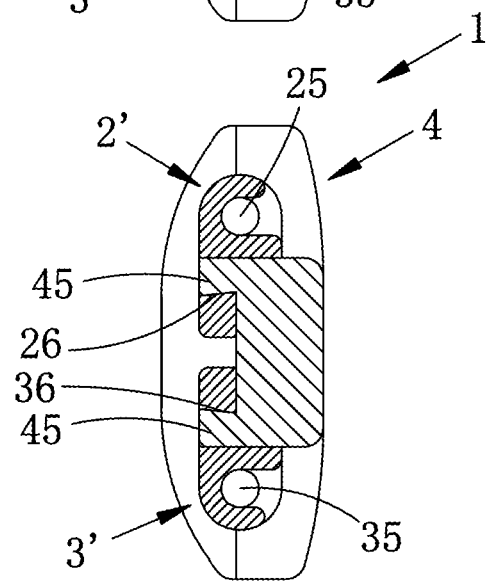
Figure 24:
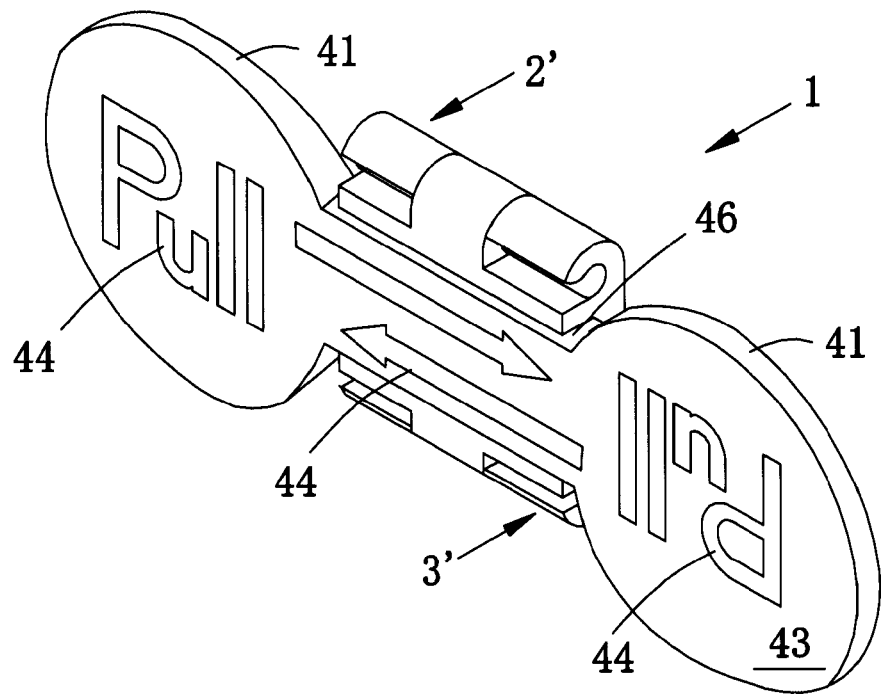
FIG. 24 shows another display example of the intermaxillary fixation releasing device 1 according to example 3 of the present invention.

The intermaxillary fixation releasing device 1 according to example 3 has a bottom surface 210 of the upper-side interlocking part 21' in contact with the center upper surface of the connector 4, an inner surface 220 of the upper-side support part 22' in contact with the intraoral surface 42 of the connector 4, an upper surface 310 of the lower-side interlocking part 31' in contact with the center lower surface of the connector, and an inner surface 320 of the lower-side support part 32' in contact with the intraoral surface 42 of the connector 4, as shown in FIG. 22(Y).

The connector attaching part 45a of the connector is thereby formed in a molten state and attached to the maxillary joint attaching part 26 and the mandibular joint attaching part 36. In this state, the upper-side interlocking part 21' and the lower-side interlocking part 31' having the insertion holes 25, 35 are disposed protruding in the vertical direction in the center of the core part 46 of the connector 4.

This configuration has the insertion hole 25 of the upper-side interlocking part 21', the insertion hole 35 of the lower-side interlocking part 31', and the connector 4 positioned in substantially the same plane. Therefore, in a state in which the intermaxillary fixation releasing device is mounted and fastened shut with a wire, the intermaxillary fixation releasing device can be prevented from deforming due to the tensile force of the wire. The separation of the maxillary joint 2', the mandibular joint 3', and the elastomer connector 4 can be facilitated by preventing the intermaxillary fixation releasing device 1 from deforming. The joining strength between the maxillary joint attaching part 26 and the connector attaching part 45a, and the joining strength between the mandibular joint attaching part 36 and the connector attaching part 45a can be adjusted by adjusting the slope of the connector attaching part 45a, and the maxillary joint attaching part 26 and the mandibular joint attaching part 36, as shown in the cross-sectional view of FIG. 23.

As an example of the manufacturing method of the present example 3, the maxillary joint 2' and the mandibular joint 3' are formed as primary molded articles during manufacture in the same manner as examples 1 and 2, the maxillary joint and the mandibular joint are inserted into a metal mold for secondary molding, an elastomer used as the resin for secondary molding is injected into the metal mold for secondary molding (including the space in which the maxillary joint mounting part 26 and the mandibular joint mounting part 36 are formed as primary molded articles), and the connector 4 is molded to obtain the intermaxillary fixation releasing device 1.

The intermaxillary fixation releasing device according examples 1 through 3 described above has the following effects.

The intermaxillary fixation releasing device 1 is manufactured under constant quality control, and is manufactured in a state in which the maxillary joint 2, the mandibular joint 3, and the connector 4 are fixed. Therefore, the intermaxillary fixation releasing device 1 can be provided as a ready-made product, and the practitioner is not required to fabricate the intermaxillary fixation releasing device 1. Accordingly, labor of the practitioner can be reduced.

An intermaxillary fixation force is applied, since the maxillary joint 2 and the mandibular joint 3 are fixed to the connector 4, and the tensile strength can be supported. Sufficient intermaxillary fixation force can be applied because there is no need to consider releasing the intermaxillary fixation during mounting.

Adjustment of the intermaxillary fixation force can be carried out adjusting the length of the ligature wire 8. Also, there is no need to confirm whether the intermaxillary fixation can be removed and to make an adjustment. Accordingly, there is no need to make an adjustment outside the oral cavity of the patient and preparation is not required.

When the intermaxillary fixation releasing device 1 is mounted, the maxillary joint 2 and the mandibular joint 3 are fixed to the connector 4, the maxillary joint 2 is connected to the intramaxillary fixation means 7 of the upper jaw via the ligature wire 8 without giving priority to releasing the intermaxillary fixation, and the mandibular joint 3 is connected to the intramaxillary fixation means 7 of the lower jaw via the ligature wire 8. The required intermaxillary fixation force can be applied by adjusting the length of the ligature wire 8. When the intermaxillary fixation is removed, the holding part 41 of the connector 4 is pulled outward from the mouth without relation to the intramaxillary fixation means 7 and the ligature wire 8, whereby the maxillary joint 2, the mandibular joint 3, and the connector 4 separate from each other and the intermaxillary fixation is removed. The intermaxillary fixation can be mounted without consideration for releasing the intermaxillary fixation, the intermaxillary fixation can be removed without relation to the strength of the intermaxillary fixation force. Accordingly, the mounting and adjustment of the intermaxillary fixation releasing device 1 can be carried out in a simple manner and without regard to the skill and experience of the practitioner.

The adjustment of the intermaxillary fixation force is carried out by adjusting the length of the ligature wire 8. Intraoral adjustment can be readily carried out because the same intermaxillary fixation means as used conventionally can be used to adjust the ligature wire 8.

The intermaxillary fixation releasing device 1 is mounted between the upper and lower jaws via the ligature wire 8. The maxillary joint 2 is connected to the intramaxillary fixation means 7 of the upper jaw via the ligature wire 8, and the mandibular joint 3 is connected to the intramaxillary fixation means 7 of the lower jaws via the ligature wire 8. The intramaxillary fixation means 7 can be used for mounting in the same manner as conventional intermaxillary fixation by merely interposing the intermaxillary fixation releasing device 1.

The intermaxillary fixation releasing device 1 is interposed at a midway point in the ligature wire 8 and can be mounted without regard to the type of intramaxillary fixation means 7. The intermaxillary fixation releasing device 1 can be mounted not only when the intramaxillary fixation means 7 uses the teeth as the fixation source 9, but also when the intramaxillary fixation means 7 does not uses the teeth as the fixation source 9. Therefore, the intermaxillary fixation releasing device 1 can be mounted in a patient whose teeth are not healthy and cannot be used as the fixation source 9.

The intermaxillary fixation releasing device 1 is interposed at a midway point in the ligature wire 8, and the same ligature wire 8 that is used for conventional intermaxillary fixation can be used. Therefore, the intermaxillary fixation releasing device 1 can be mounted even when there are individual differences in the state of the teeth, gums, and other factors. The range of application is considerable and mounting and intermaxillary fixation removal is possible even with individual differences.

The intermaxillary fixation releasing device 1 may be mounted by connecting the maxillary joint 2 to the intramaxillary fixation means 7 of the upper jaw via the ligature wire 8 and connecting the mandibular joint 3 to the intramaxillary fixation means 7 of the lower jaw via the ligature wire 8. The length of the ligature wire 8 can be adjusted in the same manner as conventional intermaxillary fixation means by adjusting the length of the ligature wire 8. Accordingly, intraoral mounting and adjustment can be readily shortened, and the burden on the patient can be reduced.

The intermaxillary fixation releasing device 1 is mounted on the buccal side of the teeth or the bone on which the intramaxillary fixation means 7 is mounted. The intermaxillary fixation releasing device 1 is mounted between the upper and lower jaws via the ligature wire 8. Therefore, the intermaxillary fixation releasing device 1 is mounted so as to make contact with the labial and buccal sides of the teeth and is accordingly less liable to make contact with the intraoral structure. The intermaxillary fixation releasing device 1 has a small, thin shape, and the connector 4 is formed from a soft resin, and is therefore less liable to damage intraoral structures, and discomfort is reduced. Therefore, the burden on the patient can be reduced.

When the connector 4 is pulled outward from the mouth in the mounted state of the intermaxillary fixation releasing device 1, the force applied by finger manipulation acts as a force for peeling away the counterpart surfaces of the maxillary joint 2 and the connector 4 as well as the mandibular joint 3 and the connector 4. When the counterpart surfaces peel away, the maxillary joint 2, the mandibular joint 3 and the connector 4 separate from each other, and the intermaxillary fixation is removed. Accordingly, intermaxillary fixation can be removed in a very short time without the use of a special tool.

Intermaxillary fixation can be removed without the use of a special tool by pulling the connector 4 outward from the mouth in the mounted state of the intermaxillary fixation releasing device 1. Therefore, intermaxillary fixation can be removed by pulling the connector 4 outward from the mouth even when a person without any knowledge of intermaxillary fixation removal encounters a patient with a blocked respiratory tract. Therefore, the possibility that the intermaxillary fixation can be removed can be increased. Also, the patient himself/herself can remove the intermaxillary fixation if required.

The intermaxillary fixation releasing device 1 is manufactured in a state in which the maxillary joint 2, the mandibular joint 3, and the connector 4 are fixed. Therefore, an intermaxillary fixation releasing device 1 manufactured under constant quality control can be provided to the practitioner. The practitioner is not required to make adjustments related to intermaxillary fixation removal. Accordingly, intermaxillary fixation can be carried out so that intermaxillary fixation removal can be reliably moved with a constant force regardless of the skill and experience of the practitioner.

The intermaxillary fixation releasing device 1 is mounted on the buccal side of the teeth or bone on which the intramaxillary fixation means 7 is mounted. The intermaxillary fixation releasing device 1 is mounted between the upper and lower jaws via the ligature wire 8. The intermaxillary fixation releasing device 1 is hidden by the lips. The intermaxillary fixation releasing device 1 can be extraorally confirmed from the slightly opened lips of the patient. Accordingly, it can be readily understood that the intermaxillary fixation can be removed by pulling the connector 4, and the possibility of removal can be increased.

It is possible to display on the holding part 41 "PULL" or the like (e.g., see FIG. 2) indicating that a pulling action is to be performed, and an arrow or the like indicating the pull direction, as a display part 44 for displaying characters, drawings, symbols, or the like for intermaxillary fixation releasing instructions or other information on the extraoral surface 43 of the connector 4. A person without any knowledge of intermaxillary fixation removal can thereby see these displays, the method for releasing the intermaxillary fixation can be readily understood, and the possibility that the intermaxillary fixation can be removed is increased.

When the intermaxillary fixation is removed, the procedure can be carried out without the use of wire-cutting scissors or other special tools. Accordingly, the intermaxillary fixation can be safely released because a dangerous tool that injures the patient is not required to be inserted into the oral cavity.

On the other hand, when the fixation is to be released by a person who knows the conventional method for releasing an intermaxillary fixation but not the release method of the present invention, the fixation can be released using a method in which wire-cutting scissors are used. Therefore, the fixation can be released by employing an ordinary release method that uses wire-cutting scissors, which such a person is accustomed to using.

The upper-side support part 22 is provided to the maxillary joint 2, and the lower-side support part 32 is provided to the mandibular joint 3, whereby the surface area of the maxillary joint 2 and the mandibular joint 3 can be increased. Therefore, the surface area of the counterpart surfaces of the maxillary joint 2 and the connector 4 as well as the mandibular joint 3 and the connector 4 can be increased and adhesive strength can be assured.

The convexity 23 and the concavity 24 are provided to the upper-side support part 22, and the convexity 23 and the concavity 24 are provided to the lower-side support part 32, whereby the surface area of the maxillary joint 2 and the mandibular joint 3 can be increased. Accordingly, the surface area of the counterpart surfaces of the maxillary joint 2 and the connector 4 as well as the mandibular joint 3 and the connector 4 can be increased, adhesive strength can be assured, and intermaxillary fixation force can be exerted. Also, the maxillary joint 2, the mandibular joint 3, and the connector 4 are interlocked in a hook-shape in the convexity 23 and the concavity 24. When an external force acts to separate the maxillary joint 2 and the mandibular joint 3 from the connector 4, the interlocking force that operates against the external force is exerted by the portion interlocked in a hook-shape, and an intermaxillary fixation force can be exerted.

The holding part 41 is formed on the two sides of the connector 4; the intermaxillary fixation releasing device is disassembled and the intermaxillary fixation can be released by manipulating one of the two holding parts 41 and pulling the connector 4. Therefore, the intermaxillary fixation can be reliably released even when one of the holding parts 41 is damaged so that the connector 4 cannot be pulled, because the other holding part 41 can be manipulated.

The ligature wire 8 is not required to be severed in the case that the intermaxillary fixation is to be released. Therefore, shards or the like of the ligature wire 8 are less liable to enter of the body of the patient when the intermaxillary fixation is released and there is little possibility of compromising the health of the patient.

Embodiments are not limited to those described above, and there follow modifications that can be made.

The connector 4 can be brought into contact with the maxillary joint 2 and the mandibular joint 3, and can be formed without the use of an upper-side support part 22 and a lower-side support part 32.

The connector 4 may have the maxillary joint 2' and the mandibular joint 3' attached together. Therefore, the styrene-based elastomer may be caused to fill depressions formed in the maxillary joint 2' and the mandibular joint 3' to form the connector 4 (see FIG. 25).

The concavity 24 and the convexity 23 may be configured as a convex strip, a concave strip, a depression, a protrusion, or another shape other than the constricted portion. Using such shapes allows the surface area of the counterpart surfaces to be increased, adequate adhesive strength to be obtained, and an intermaxillary fixation force to be exhibited.

Figure 25:
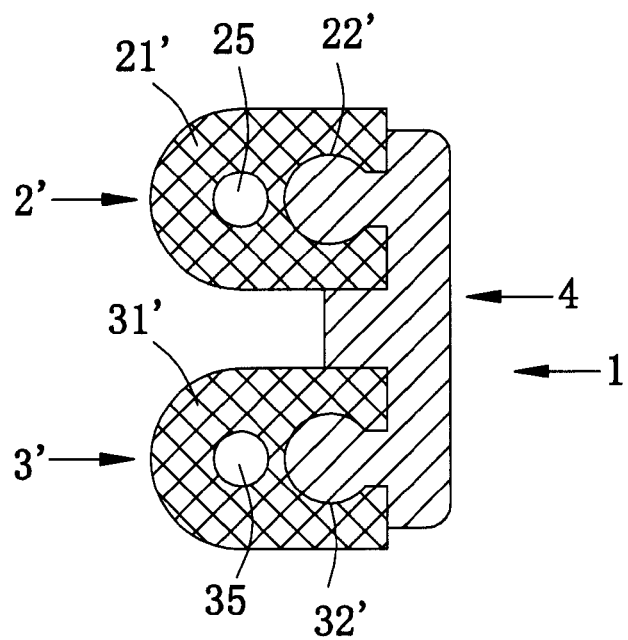
FIG. 25 is an enlarged end surface view of the intermaxillary fixation releasing device 1 according to another example of the present invention in a state sectioned in the height direction.

The upper-side support part 22' formed on the maxillary joint 2' is not required to be protrudingly provided to the upper-side interlocking part 21', and may be formed so that a portion of the upper-side interlocking part 21' is a depressed shape (see FIG. 25). The same applies to the lower-side support part 32' formed on the mandibular joint 3'. The intermaxillary fixation releasing device 1 can thereby be imparted with a thin profile.

The maxillary joint 2, the mandibular joint 3, and the connector 4 can be formed from an antibacterial resin. In this case, the mounted intermaxillary fixation releasing device 1 can be kept hygienic.

The maxillary joint 2, the mandibular joint 3, and the connector 4 can be formed from resins of a variety of colors. For example, making the intermaxillary fixation releasing device 1 transparent, white, or another color can reduce mental stress on the part of the patient by having the device be no more noticeable than necessary when mounted on the front teeth or the like. Also, using a noticeable color in an intermaxillary fixation releasing device 1 mounted on the molars allows visibility to be increased and safety to be assured.

The invention claimed is:

1. A disposable device for removal of an intermaxillary fixation, said device comprising:
    a maxillary joint composed of a first synthetic resin;
    a mandibular joint composed of a second synthetic resin; and
    a connector composed of an elastomer, wherein
    the maxillary joint is provided with an upper-side interlocking part and an upper-side support part,
    the mandibular joint is provided with a lower-side interlocking part and a lower-side support part,
    the elastomer forming the connector is incompatible with the first synthetic resin and the second synthetic resin,
    the upper-side support part and the lower-side support part are embedded in a core part of the connector, and the upper-side support part and the lower-side support part are joined,
    the connector comprises the core part formed in a central region of the connector and a holding part formed at opposing ends of the core part, in a horizontal direction, of the connector, and,
    the holding part of said disposable device is for grasping and pulling the opposing ends of the connector.

2. The disposable device for removal of intermaxillary fixation as recited in claim 1, wherein
    the upper-side support part is in contact with the lower-side support part, the upper-side support part and the lower-side support part are embedded in the core part of the connector, and the upper-side support part and the lower-side support part are joined.

3. The disposable device for removal of intermaxillary fixation as recited in claim 1, characterized in having a configuration in which the holding part is a tongue-shaped holding part and is formed at the opposing ends, in a horizontal direction, of the core part.

4. The disposable device for removal of intermaxillary fixation as recited in claim 1, characterized in that an extraoral surface of the connector is provided with a display part for displaying characters, drawings, symbols, or the like for intermaxillary fixation releasing instructions or other information.

5. The disposable device for removal of intermaxillary fixation as recited in claim 1 or 4, characterized in having a configuration in which the connector is formed from the core part and a tongue-shaped holding part at the opposing ends of the core part, wherein
    an extraoral surface of the connector is provided with a display part for displaying characters, drawings, symbols, or the like for intermaxillary fixation releasing instructions or other information.

* * * * *